US007479284B2

(12) United States Patent  
Schetters et al.

(10) Patent No.: US 7,479,284 B2  
(45) Date of Patent: Jan. 20, 2009

(54) *BABESIA CANIS* VACCINE

(75) Inventors: Theodorus Petrus Maria Schetters, Cuyk (NL); Bernard Pierre Dominique Carcy, Montpellier (FR); Pascal Robert Drakulovski, Montpellier (FR); Andre Francois Gorenflot, Montpellier (FR)

(73) Assignee: Intervet International B.V., Boxmeer (NL)

( * ) Notice: Subject to any disclaimer, the term of this patent is extended or adjusted under 35 U.S.C. 154(b) by 399 days.

(21) Appl. No.: 11/249,112

(22) Filed: Oct. 11, 2005

(65) Prior Publication Data

US 2008/0003223 A1    Jan. 3, 2008

Related U.S. Application Data

(62) Division of application No. 10/087,573, filed on Feb. 28, 2002, now Pat. No. 7,090,849.

(30) Foreign Application Priority Data

Mar. 6, 2001    (EP)    .................................. 01200816

(51) Int. Cl.  
*A61K 39/018* (2006.01)  
*C07H 21/04* (2006.01)  
*C12P 21/04* (2006.01)  
*C12N 15/09* (2006.01)

(52) U.S. Cl. .............. 424/270.1; 424/265.1; 424/190.1; 435/69.1; 536/23.1

(58) Field of Classification Search .............. 424/270.1, 424/265.1, 190.1; 435/69.1; 536/23.1  
See application file for complete search history.

(56) References Cited

U.S. PATENT DOCUMENTS

| 6,045,086 A | 4/2000 | Jeans |
| 6,045,806 A | 4/2000 | Akzo |
| 7,090,849 B2 | 8/2006 | Akzo |

FOREIGN PATENT DOCUMENTS

| EP | 0 691 131 A1 | 1/1996 |
| EP | 1 050 541 A1 | 11/2000 |

OTHER PUBLICATIONS

Schetters et al Parasitol. Today (11, No. 12, 456-62, 1995).*  
Schetters et al 1992 (Parasite Immunology 1992, 14(3) 295-305 abstract only).*  
Schetters et al, Veterinary Parasitology, (Apr. 1994) vol. 52, No. 3-4, pp. 219-33.*  
Ellis, Ronald W, Ph.D. Chapter 29, New Technologies for Making Vaccines, Vaccines, WB Saunders Co., 1988, pp. 568-575.*  
Boslego John W. et al 1991 Chapter 17, pp. 211-223, Vaccines and Immunotherapy, SJ. Cruz, ed, Pergamon Press, New York.*  
Colman et al, Research in Immunology, 1994; 145(1): 33-36).*  
Abaza et al, Journal of Protein Chemistry, 1992, vol. 11, No. 5, pp. 433-444.*  
Lederman et al (Molecular Immunology 28:1171-1181, 1991).*  
Li et al (Proc. Natl. Acad. Sci. USA 77:3211-3214, 1980).*  
Schetters, T.P.M. et al.: "Can babesia infections be used as a model for cerebral malaria?" Parasitology Today (Dec. 1999) V15, N12, pp. 492-497.  
Grande N., et al.: "Comparison between aseric and seric culture-derived exoantigens . . . " Parasitology International, Elsevier Science, (Dec. 1998) V47, N4, pp. 269-279, NL.  
Carret, C. et al.:"Babesia canis canis, Babesia canis vogeli, Babesia canis rossi: Differentiation of the . . . " J. of Eukaryotic Microbiology, (May 1999) V46, N3, pp. 298-303.  
Carcy, B. et al.: "A 37-kilodalton glycoprotein of Babesia divergens is . . . " Infection and Immunity, American Society for Microbiology (Mar. 1995) V63, N3, pp. 811-817, USA.  
Carret, C. et al.: "Characterization and molecular cloning of an adenosine kinase from Babesia canis rossi" European Journal of Biochemistry (Nov. 1999) V265, N3, pp. 1015-1021.  
Kulakov, et al.: "Comparatiave analysis of Brucella antigen by . . . " Molekulyarnaya Genetika, Mikrobiologiya i Virusologiya (1998) (2), 7-13 (abstract only).  
Schetters, et al: "Vaccination of dogs against Babesia . . . " Parasite Immunology (1992) 14(3) 295-305 (abstract only).  
Burgess, et al.: "Possibile Dissociation of the Heparin-binding and Mitogenic Activities . . . " The Journal of Cell Biology, 111: 2129-2138 (1990).

* cited by examiner

*Primary Examiner*—Robert B Mondesi  
*Assistant Examiner*—Padma V Baskar  
(74) *Attorney, Agent, or Firm*—Aaron L. Schwartz; William M. Blackstone

(57) ABSTRACT

The present invention relates to nucleic acid sequences encoding novel *Babesia canis* associated proteins and to cDNA fragments, recombinant DNA molecules and live recombinant carriers comprising these sequences. Furthermore, the invention relates to host cells comprising such nucleic acid sequences, cDNA fragments, recombinant DNA molecules and live recombinant carriers. Also, the invention relates to proteins encoded by these nucleotide sequences, to vaccines for combating *Babesia canis* infections comprising these proteins or genetic material encoding these proteins and methods for the preparation of vaccines. Another embodiment of the invention relates to these *Babesia canis* associated proteins for use in vaccines and to the use of the *Babesia canis* associated proteins in the manufacture of vaccines. Finally the invention relates to diagnostic tools for the detection of *Babesia canis* associated nucleic acid sequences, for the detection of *Babesia canis* associated antigens and for the detection of antibodies against *Babesia canis* associated antigenic material.

9 Claims, 11 Drawing Sheets

SEQ. ID NO. 1
EcoRI
gaattcggcacgagccctgctatactgtgctttgcaactaactccatcgtaataatttaatataataataaa    72

```
         M   E   S   T   S   T   T   T   N   F   V   A   E   N   R   P   T      17
      gg ATG GAG TCG ACA TCA ACA ACG ACC AAC TTT GTT GCC GAG AAC CGT CCC ACC    125

F   G   E   T   F   D   V   M   R   E   A   L   L   R   V   K   S   S      35
     TTT GGT GAG ACG TTT GAT GTG ATG AGG GAA GCT TTG CTT CGT GTA AAG TCC TCT    179

E   R   L   A   M   L   R   A   L   A   G   M   C   G   H   R   V   L      53
     GAA CGC TTG GCA ATG CTC AGA GCG CTT GCA GGA ATG TGC GGT CAC CGC GTC CTT    233

P   G   T   G   A   S   A   I   A   A   T   V   T   P   K   G   A   S      71
     CCT GGC ACT GGT GCT TCT GCG ATA GCG GCA ACG GTA ACC CCA AAG GGG GCT TCG    287

M   K   L   K   P   P   R   P   Q   S   T   K   S   P   E   L   R   E      89
     ATG AAG CTT AAA CCA CCG CGT CCG CAG TCA ACG AAG TCT CCG GAG CTC AGG GAG    341

L   S   R   K   I   R   E   M   N   K   T   I   S   Q   E   S   A   R     107
     CTG TCA CGG AAG ATT CGC GAA ATG AAT AAG ACT ATA AGT CAG GAA TCA GCT CGG    395

V   N   H   R   L   P   E   G   H   P   L   L   E   K   R   A   E   Y     125
     GTA AAC CAC CGG TTG CCG GAA GGC CAC CCT CTC TTA GAG AAG CGG GCA GAA TAT    449

F   R   H   L   R   S   L   K   S   Q   G   V   N   R   L   I   *         141
     TTT CGT CAC CTT AGA TCT CTT AAG AGC CAA GGA GTC AAT AGA CTC ATC TAA G      501
```
aaggcactacgtaggtaccgtgcctctatgaggaatacgaaccgactagtgcacaatagacgaccagttcta    573
ccaaaggtagagcctgactctaatctaccattcggccagcgacggagtcgcatgacaacgtggaatcttaga    645
ccacgccggacgggttatccgtcaaatggtactttggcagttacggaactcctgatctcgatttatagatca    717
aacttctacaccttgaaggtggtcgaggaagggagatgtacgtgctgcaacacccataaggagcaagctttg    789
ctactcctatccggttacctccagctatatcgtgcactgcactcagttggaaggtctgtattcgtagaatac    861
tgcaaaaccaggatatgcgtcgaggcacgcctcaccggactacgtcgagggtgaccctaacgggctgctga    933
actaggttcagccagcgcttcctgtgagtatgtcattccgggtccttcggggcccgggccagtttcgactgg   1005
tgtaggtttgccctactagagtacttgcgacgccgaagcgcctccgttcaaaagaacgcgcaagccctagca   1077
gagaaatgcgagggcatgactcttcgagtcaaaaaaaaaaaaaaaaaaaaaactcgag                 1135
                                                        XhoI

Figure 2

SEQ. ID NO. 3  EcoRI
gaattcggcacgagccctgctatactgtgctttgcaactaactccatcgtaataatttaatataataataaa 72

```
                 M   E   S   T   S   T   T   T   N   F   V   A   E   N   R   P   T    17
              gg ATG GAG TCG ACA TCA ACA ACG ACC AAC TTT GTT GCC GAG AAC CGT CCC ACC 125

F   G   E   T   F   D   V   M   R   E   A   L   L   R   V   K   S   S    35
             TTT GGT GAG ACG TTT GAT GTG ATG AGG GAA GCT TTG CTT CGT GTA AAG TCC TCT 179

E   R   L   A   M   L   R   A   L   A   G   M   C   G   H   R   V   L    53
             GAA CGC TTG GCA ATG CTC AGA GCG CTT GCA GGA ATG TGC GGT CAC CGC GTC CTT 233

P   G   T   G   A   S   A   I   A   A   T   V   T   P   K   G   A   S    71
             CCT GGC ACT GGT GCT TCT GCG ATA GCG GCA ACG GTA ACC CCA AAG GGG GCT TCG 287

M   K   L   K   P   P   R   P   Q   S   T   K   S   P   E   L   R   E    89
             ATG AAG CTT AAA CCA CCG CGT CCG CAG TCA ACG AAG TCT CCG GAG CTC AGG GAG 341

L   S   R   K   I   R   E   M   N   K   T   I   S   Q   E   S   A   R   107
             CTG TCA CGG AAG ATT CGC GAA ATG AAT AAG ACT ATA AGT CAG GAA TCA GCT CGG 395

V   N   H   R   L   P   E   G   H   P   L   E   K   R   A   E   Y   125
             GTA AAC CAC CGG TTG CCG GAA GGC CAC CCT CTC TTA GAG AAG CGG GCA GAA TAT 449

F   V   T   L   D   L   L   R   A   K   E   S   I   D   S   S   K   K   143
         (T) TTC GTC ACC TTA GAT CTC TTA AGA GCC AAG GAG TCA ATA GAC TCA TCT AAG AAG 504

A   L   R   R   Y   R   A   S   M   R   N   T   N   R   L   V   H   N   161
             GCA CTA CGT AGG TAC CGT GCC TCT ATG AGG AAT ACG AAC CGA CTA GTG CAC AAT 558

R   R   P   V   L   P   K   V   E   P   D   S   N   L   P   F   G   Q   179
             AGA CGA CCA GTT CTA CCA AAG GTA GAG CCT GAC TCT AAT CTA CCA TTC GGC CAG 612

R   R   S   R   M   T   T   W   N   L   R   P   R   R   T   G   Y   P   197
             CGA CGG AGT CGC ATG ACA ACG TGG AAT CTT AGA CCA CGC CGG ACG GGT TAT CCG 666

S   N   G   T   L   A   V   T   E   L   L   I   S   I   Y   R   S   N   215
             TCA AAT GGT ACT TTG GCA GTT ACG GAA CTC CTG ATC TCG ATT TAT AGA TCA AAC 720

F   Y   T   L   K   V   V   E   E   G   R   C   T   C   C   N   T   H   233
             TTC TAC ACC TTG AAG GTG GTC GAG GAA GGG AGA TGT ACG TGC TGC AAC ACC CAT 774

K   E   Q   A   L   L   L   S   G   Y   L   Q   L   Y   R   A   L   251
             AAG GAG CAA GCT TTG CTA CTC CTA TCC GGT TAC CTC CAG CTA TAT CGT GCA CTG 828

H   S   V   G   R   S   V   F   V   E   Y   C   K   T   R   I   C   V   269
             CAC TCA GTT GGA AGG TCT GTA TTC GTA GAA TAC TGC AAA ACC AGG ATA TGC GTC 882

E   A   R   L   T   G   L   R   P   R   V   T   L   T   G   C   *       285
             GAG GCA CGC CTC ACC GGA CTA CGT CCG AGG GTG ACC CTA ACG GGC TGC TGA A   934
             ctaggttcagccagcgcttcctgtgagtatgtcattccgggtccttcggggcccgggccagtttcgactggt 1006
             gtaggtttgccctactagagtacttgcgacgccgaagcgcctccgttcaaaagaacgcgcaagccctagcag 1078
             agaaatgcgagggcatgactcttcgagtcaaaaaaaaaaaaaaaaaaaaactcgag              1135
                                                                         XhoI
```

Figure 3

**Inhibition *in vitro B. canis* A**

- CONT
- T0
- orf2
- Bcvir15
- GST

**Inhibition *in vitro B. canis* B**

- CONT
- T0
- orf2
- Bcvir15
- GST

**Inhibition *in vitro B. rossi* M**

- CONT
- T0
- orf2
- Bcvir15
- GST

Figure 17

SEQUENCE LISTING

```
<160> NUMBER OF SEQ ID NOS: 17

<210> SEQ ID NO 1
<211> LENGTH: 1135
<212> TYPE: DNA
<213> ORGANISM: Babesia canis
<220> FEATURE:
<221> NAME/KEY: CDS
<222> LOCATION: (75)..(500)

<400> SEQUENCE: 1
gaattcggca cgagccctgc tatactgtgc tttgcaacta actccatcgt aataatttaa      60
tataataata aagg atg gag tcg aca tca aca acg acc aac ttt gtt gcc      110
              Met Glu Ser Thr Ser Thr Thr Thr Asn Phe Val Ala
                1               5                   10 gag aac cgt ccc acc ttt ggt gag acg ttt gat gtg atg agg gaa gct      158
Glu Asn Arg Pro Thr Phe Gly Glu Thr Phe Asp Val Met Arg Glu Ala
            15                  20                  25 ttg ctt cgt gta aag tcc tct gaa cgc ttg gca atg ctc aga gcg ctt      206
Leu Leu Arg Val Lys Ser Ser Glu Arg Leu Ala Met Leu Arg Ala Leu
        30                  35                  40 gca gga atg tgc ggt cac cgc gtc ctt cct ggc act ggt gct tct gcg      254
Ala Gly Met Cys Gly His Arg Val Leu Pro Gly Thr Gly Ala Ser Ala
    45                  50                  55                  60 ata gcg gca acg gta acc cca aag ggg gct tcg atg aag ctt aaa cca      302
Ile Ala Ala Thr Val Thr Pro Lys Gly Ala Ser Met Lys Leu Lys Pro
                65                  70                  75 ccg cgt ccg cag tca acg aag tct ccg gag ctc agg gag ctg tca cgg      350
Pro Arg Pro Gln Ser Thr Lys Ser Pro Glu Leu Arg Glu Leu Ser Arg
            80                  85                  90 aag att cgc gaa atg aat aag act ata agt cag gaa tca gct cgg gta      398
Lys Ile Arg Glu Met Asn Lys Thr Ile Ser Gln Glu Ser Ala Arg Val
        95                  100                 105 aac cac cgg ttg ccg gaa ggc cac cct ctc tta gag aag cgg gca gaa      446
Asn His Arg Leu Pro Glu Gly His Pro Leu Leu Glu Lys Arg Ala Glu
```

```
              110                 115                 120
tat ttt cgt cac ctt aga tct ctt aag agc caa gga gtc aat aga ctc      494
Tyr Phe Arg His Leu Arg Ser Leu Lys Ser Gln Gly Val Asn Arg Leu
125                 130                 135                 140 atc taa gaaggcacta cgtaggtacc gtgcctctat gaggaatacg aaccgactag       550
Ile tgcacaatag acgaccagtt ctaccaaagg tagagcctga ctctaatcta ccattcggcc    610
agcgacggag tcgcatgaca acgtggaatc ttagaccacg ccggacgggt tatccgtcaa    670
atggtacttt ggcagttacg gaactcctga tctcgattta tagatcaaac ttctacacct    730
tgaaggtggt cgaggaaggg agatgtacgt gctgcaacac ccataaggag caagctttgc    790
tactcctatc cggttacctc cagctatatc gtgcactgca ctcagttgga aggtctgtat    850
tcgtagaata ctgcaaaacc aggatatgcg tcgaggcacg cctcaccgga ctacgtccga    910
gggtgaccct aacgggctgc tgaactaggt tcagccagcg cttcctgtga gtatgtcatt    970
ccgggtcctt cggggcccgg ccagtttcg actggtgtag gtttgcccta ctagagtact    1030
tgcgacgccg aagcgcctcc gttcaaaaga acgcgcaagc cctagcagag aaatgcgagg   1090
gcatgactct tcgagtcaaa aaaaaaaaaa aaaaaaaaac tcgag                  1135

<210> SEQ ID NO 2
<211> LENGTH: 141
<212> TYPE: PRT
<213> ORGANISM: Babesia canis

<400> SEQUENCE: 2

Met Glu Ser Thr Ser Thr Thr Thr Asn Phe Val Ala Glu Asn Arg Pro
1               5                   10                  15

Thr Phe Gly Glu Thr Phe Asp Val Met Arg Glu Ala Leu Leu Arg Val
                20                  25                  30

Lys Ser Ser Glu Arg Leu Ala Met Leu Arg Ala Leu Ala Gly Met Cys
            35                  40                  45

Gly His Arg Val Leu Pro Gly Thr Gly Ala Ser Ala Ile Ala Ala Thr
        50                  55                  60

Val Thr Pro Lys Gly Ala Ser Met Lys Leu Lys Pro Pro Arg Pro Gln
65                  70                  75                  80

Ser Thr Lys Ser Pro Glu Leu Arg Glu Leu Ser Arg Lys Ile Arg Glu
                85                  90                  95

Met Asn Lys Thr Ile Ser Gln Glu Ser Ala Arg Val Asn His Arg Leu
            100                 105                 110

Pro Glu Gly His Pro Leu Leu Glu Lys Arg Ala Glu Tyr Phe Arg His
        115                 120                 125

Leu Arg Ser Leu Lys Ser Gln Gly Val Asn Arg Leu Ile
    130                 135                 140

<210> SEQ ID NO 3
<211> LENGTH: 1134
<212> TYPE: DNA
<213> ORGANISM: Babesia canis
<220> FEATURE:
<221> NAME/KEY: CDS
<222> LOCATION: (75)..(929)

<400> SEQUENCE: 3
gaattcggca cgagccctgc tatactgtgc tttgcaacta actccatcgt aataatttaa    60
tataataata aagg atg gag tcg aca tca aca acg acc aac ttt gtt gcc    110
              Met Glu Ser Thr Ser Thr Thr Thr Asn Phe Val Ala
              1               5                   10
```

| | | |
|---|---|---|
| gag aac cgt ccc acc ttt ggt gag acg ttt gat gtg atg agg gaa gct<br>Glu Asn Arg Pro Thr Phe Gly Glu Thr Phe Asp Val Met Arg Glu Ala<br>15　　　　　　　　20　　　　　　　　25 | | 158 |
| ttg ctt cgt gta aag tcc tct gaa cgc ttg gca atg ctc aga gcg ctt<br>Leu Leu Arg Val Lys Ser Ser Glu Arg Leu Ala Met Leu Arg Ala Leu<br>30　　　　　　　　35　　　　　　　　40 | | 206 |
| gca gga atg tgc ggt cac cgc gtc ctt cct ggc act ggt gct tct gcg<br>Ala Gly Met Cys Gly His Arg Val Leu Pro Gly Thr Gly Ala Ser Ala<br>45　　　　　　　50　　　　　　　　55　　　　　　　　60 | | 254 |
| ata gcg gca acg gta acc cca aag ggg gct tcg atg aag ctt aaa cca<br>Ile Ala Ala Thr Val Thr Pro Lys Gly Ala Ser Met Lys Leu Lys Pro<br>　　　　　65　　　　　　　　70　　　　　　　　75 | | 302 |
| ccg cgt ccg cag tca acg aag tct ccg gag ctc agg gag ctg tca cgg<br>Pro Arg Pro Gln Ser Thr Lys Ser Pro Glu Leu Arg Glu Leu Ser Arg<br>80　　　　　　　　85　　　　　　　　90 | | 350 |
| aag att cgc gaa atg aat aag act ata agt cag gaa tca gct cgg gta<br>Lys Ile Arg Glu Met Asn Lys Thr Ile Ser Gln Glu Ser Ala Arg Val<br>　　　95　　　　　　　　100　　　　　　　105 | | 398 |
| aac cac cgg ttg ccg gaa ggc cac cct ctc tta gag aag cgg gca gaa<br>Asn His Arg Leu Pro Glu Gly His Pro Leu Leu Glu Lys Arg Ala Glu<br>110　　　　　　　115　　　　　　　120 | | 446 |
| tat ttc gtc acc tta gat ctc tta aga gcc aag gag tca ata gac tca<br>Tyr Phe Val Thr Leu Asp Leu Leu Arg Ala Lys Glu Ser Ile Asp Ser<br>125　　　　　　　130　　　　　　　135　　　　　　　140 | | 494 |
| tct aag aag gca cta cgt agg tac cgt gcc tct atg agg aat acg aac<br>Ser Lys Lys Ala Leu Arg Arg Tyr Arg Ala Ser Met Arg Asn Thr Asn<br>　　　　　145　　　　　　　150　　　　　　　155 | | 542 |
| cga cta gtg cac aat aga cga cca gtt cta cca aag gta gag cct gac<br>Arg Leu Val His Asn Arg Arg Pro Val Leu Pro Lys Val Glu Pro Asp<br>160　　　　　　　165　　　　　　　170 | | 590 |
| tct aat cta cca ttc ggc cag cga cgg agt cgc atg aca acg tgg aat<br>Ser Asn Leu Pro Phe Gly Gln Arg Arg Ser Arg Met Thr Thr Trp Asn<br>　　　175　　　　　　　180　　　　　　　185 | | 638 |
| ctt aga cca cgc cgg acg ggt tat ccg tca aat ggt act ttg gca gtt<br>Leu Arg Pro Arg Arg Thr Gly Tyr Pro Ser Asn Gly Thr Leu Ala Val<br>190　　　　　　　195　　　　　　　200 | | 686 |
| acg gaa ctc ctg atc tcg att tat aga tca aac ttc tac acc ttg aag<br>Thr Glu Leu Leu Ile Ser Ile Tyr Arg Ser Asn Phe Tyr Thr Leu Lys<br>205　　　　　　　210　　　　　　　215　　　　　　　220 | | 734 |
| gtg gtc gag gaa ggg aga tgt acg tgc tgc aac acc cat aag gag caa<br>Val Val Glu Glu Gly Arg Cys Thr Cys Cys Asn Thr His Lys Glu Gln<br>　　　　　225　　　　　　　230　　　　　　　235 | | 782 |
| gct ttg cta ctc cta tcc ggt tac ctc cag cta tat cgt gca ctg cac<br>Ala Leu Leu Leu Leu Ser Gly Tyr Leu Gln Leu Tyr Arg Ala Leu His<br>240　　　　　　　245　　　　　　　250 | | 830 |
| tca gtt gga agg tct gta ttc gta gaa tac tgc aaa acc agg ata tgc<br>Ser Val Gly Arg Ser Val Phe Val Glu Tyr Cys Lys Thr Arg Ile Cys<br>　　　255　　　　　　　260　　　　　　　265 | | 878 |
| gtc gag gca cgc ctc acc gga cta cgt ccg agg gtg acc cta acg ggc<br>Val Glu Ala Arg Leu Thr Gly Leu Arg Pro Arg Val Thr Leu Thr Gly<br>270　　　　　　　275　　　　　　　280 | | 926 |
| tgc tgaactaggt tcagccagcg cttcctgtga gtatgtcatt ccgggtcctt<br>Cys<br>285 | | 979 |
| cggggcccgg gccagtttcg actggtgtag gtttgcccta ctagagtact tgcgacgccg | | 1039 |
| aagcgcctcc gttcaaaaga acgcgcaagc cctagcagag aaatgcgagg gcatgactct | | 1099 |
| tcgagtcaaa aaaaaaaaaa aaaaaaaaac tcgag | | 1134 |

<210> SEQ ID NO 4
<211> LENGTH: 285
<212> TYPE: PRT
<213> ORGANISM: Babesia canis

<400> SEQUENCE: 4

Met Glu Ser Thr Ser Thr Thr Thr Asn Phe Val Ala Glu Asn Arg Pro
 1               5                  10                  15

Thr Phe Gly Glu Thr Phe Asp Val Met Arg Glu Ala Leu Leu Arg Val
             20                  25                  30

Lys Ser Ser Glu Arg Leu Ala Met Leu Arg Ala Leu Ala Gly Met Cys
         35                  40                  45

Gly His Arg Val Leu Pro Gly Thr Gly Ala Ser Ala Ile Ala Ala Thr
     50                  55                  60

Val Thr Pro Lys Gly Ala Ser Met Lys Leu Lys Pro Pro Arg Pro Gln
 65                  70                  75                  80

Ser Thr Lys Ser Pro Glu Leu Arg Glu Leu Ser Arg Lys Ile Arg Glu
                 85                  90                  95

Met Asn Lys Thr Ile Ser Gln Glu Ser Ala Arg Val Asn His Arg Leu
            100                 105                 110

Pro Glu Gly His Pro Leu Leu Glu Lys Arg Ala Glu Tyr Phe Val Thr
        115                 120                 125

Leu Asp Leu Leu Arg Ala Lys Glu Ser Ile Asp Ser Ser Lys Lys Ala
    130                 135                 140

Leu Arg Arg Tyr Arg Ala Ser Met Arg Asn Thr Asn Arg Leu Val His
145                 150                 155                 160

Asn Arg Arg Pro Val Leu Pro Lys Val Glu Pro Asp Ser Asn Leu Pro
                165                 170                 175

Phe Gly Gln Arg Arg Ser Arg Met Thr Thr Trp Asn Leu Arg Pro Arg
            180                 185                 190

Arg Thr Gly Tyr Pro Ser Asn Gly Thr Leu Ala Val Thr Glu Leu Leu
        195                 200                 205

Ile Ser Ile Tyr Arg Ser Asn Phe Tyr Thr Leu Lys Val Val Glu Glu
    210                 215                 220

Gly Arg Cys Thr Cys Cys Asn Thr His Lys Glu Gln Ala Leu Leu Leu
225                 230                 235                 240

Leu Ser Gly Tyr Leu Gln Leu Tyr Arg Ala Leu His Ser Val Gly Arg
                245                 250                 255

Ser Val Phe Val Glu Tyr Cys Lys Thr Arg Ile Cys Val Glu Ala Arg
            260                 265                 270

Leu Thr Gly Leu Arg Pro Arg Val Thr Leu Thr Gly Cys
        275                 280                 285

<210> SEQ ID NO 5
<211> LENGTH: 90
<212> TYPE: DNA
<213> ORGANISM: Babesia canis

<400> SEQUENCE: 5
ggatcctaat acgactcact atagggagac caccatggag tcgacatcaa caacgaccaa      60
ctttgttgcc gagaaccgtc ccacctttgg                                      90

<210> SEQ ID NO 6
<211> LENGTH: 24
<212> TYPE: DNA
<213> ORGANISM: Babesia canis -continued

```
<400> SEQUENCE: 6
gacgtttgat gtgatgaggg aagc                                              24

<210> SEQ ID NO 7
<211> LENGTH: 21
<212> TYPE: DNA
<213> ORGANISM: Babesia canis

<400> SEQUENCE: 7
aatgacatac tcacaggaag c                                                 21

<210> SEQ ID NO 8
<211> LENGTH: 20
<212> TYPE: DNA
<213> ORGANISM: Babesia canis

<400> SEQUENCE: 8
atgagtctat tgactccttg                                                   20

<210> SEQ ID NO 9
<211> LENGTH: 21
<212> TYPE: DNA
<213> ORGANISM: Babesia canis

<400> SEQUENCE: 9
agggagctgt cacggaagat t                                                 21

<210> SEQ ID NO 10
<211> LENGTH: 21
<212> TYPE: DNA
<213> ORGANISM: Babesia canis

<400> SEQUENCE: 10
atgaggaatt cgaaccgact a                                                 21

<210> SEQ ID NO 11
<211> LENGTH: 74
<212> TYPE: DNA
<213> ORGANISM: Babesia canis

<400> SEQUENCE: 11
gcagaatatt ttcgtcacct tagatctctt aagagccaag gagtcaatag actcatctaa       60
gaaggcacta cgta                                                         74

<210> SEQ ID NO 12
<211> LENGTH: 24
<212> TYPE: DNA
<213> ORGANISM: Babesia canis

<400> SEQUENCE: 12
gacgtttgat gtgatgaggg aagc                                              24

<210> SEQ ID NO 13
<211> LENGTH: 21
<212> TYPE: DNA
<213> ORGANISM: Babesia canis

<400> SEQUENCE: 13
agggagctgt cacggaagat t                                                 21

<210> SEQ ID NO 14
```

```
<211> LENGTH: 21
<212> TYPE: DNA
<213> ORGANISM: Babesia canis

<400> SEQUENCE: 14
aatgacatac tcacaggaag c                                              21

<210> SEQ ID NO 15
<211> LENGTH: 20
<212> TYPE: DNA
<213> ORGANISM: Babesia canis

<400> SEQUENCE: 15
atgagtctat tgactccttg                                                20

<210> SEQ ID NO 16
<211> LENGTH: 88
<212> TYPE: DNA
<213> ORGANISM: Babesia canis

<400> SEQUENCE: 16
ggatcctaat acgactcact atagggagac caccatggag tcgacatcaa cagaccaact     60
ttgttgccga gaaccgtccc acctttgg                                       88

<210> SEQ ID NO 17
<211> LENGTH: 22
<212> TYPE: PRT
<213> ORGANISM: Babesia canis

<400> SEQUENCE: 17

Ile Phe Val Thr Leu Asp Leu Leu Arg Ala Lys Glu Ser Ile Asp Ser
 1               5                  10                  15

Ser Lys Lys Ala Leu Arg
            20
```

BABESIA CANIS VACCINE

RELATED APPLICATIONS

This application is a divisional application of U.S. application Ser. No. 10/087,573 filed on Feb. 28, 2002, (now U.S. Pat. No. 7,090,849), which is included herein in its entirety by reference.

FIELD OF THE INVENTION

The present invention relates to nucleic acid sequences encoding novel *Babesia canis* associated proteins, to cDNA fragments, recombinant DNA molecules and live recombinant carriers comprising these sequences and to host cells comprising such nucleic acid sequences, cDNA fragments, recombinant DNA molecules and live recombinant carriers. Furthermore, the invention relates to proteins encoded by these nucleotide sequences, to vaccines for combating *Babesia canis* infections and methods for the preparation thereof, to *Babesia canis* associated antigenic material for use in vaccines and to the use of *Babesia canis* associated antigenic material in the manufacture of vaccines. Also, the invention relates to diagnostic tools for the detection of *Babesia canis* associated nucleic acid sequences, for the detection of *Babesia canis* associated antigens and for the detection of antibodies against *Babesia canis* associated antigenic material.

BACKGROUND OF THE INVENTION

Babesiosis, like malaria, is a disease which has a focal character. The reason for this is that the pathogen is transmitted by ticks that feed on a certain reservoir of parasites present in the vertebrate population. Only where ticks are present, babesiosis can occur. On balance, particularly in indigenous animals, the parasite coexists with the host without causing significant disease. In many cases babesiosis is a problem because of man's activities through inbreeding of genetic traits and/or transporting animals to unfamiliar environments where babesiosis is endemic (Callow, L. L and Dalgliesh, R. J., 1982).

In dogs the disease is caused by *B. canis* (transmitted by Dermacentor ticks), *B. rossi* (transmitted by Haemaphysalis ticks), *B. vogeli* (transmitted by Rhipicephalus ticks) and *Babesia gibsoni* (transmitted by Haemaphysalis and Rhipicephalus ticks).

Signs of disease in naturally acquired babesiosis usually begin 7-21 days after infection. These symptoms include: fever, anorexia, depression, anaemia, haemoglobinuria and rapidly developing weakness. Increased lacrimation, salivation and muscle tremor commonly occur. Nervous signs may develop in terminal infections, and death may occur when the disease is left untreated. Severe coagulation disturbances resembling disseminated intravascular coagulation (DIC) have been reported in acute *B. canis* infections. Thrombosis is not common, but small hyaline thrombi, connected with megakaryocytes have been described. It appears that these coagulation disturbances lead to increased erythrocyte-stickiness. As a result the blood passage through the microvasculature is hampered, resulting in congestion of internal organs and decreased packed cell volumes (PCV). This might impair the oxygen supply to certain tissues and subsequently lead to tissue damage as a result of anoxia. Evidence from congestion in *B. canis* infections comes from experiments in which dogs were chemotherapeutically treated. Some of these animals restore the packed cell volume in two days from 25-35%, which is associated with shrinkage of the spleen to normal measures.

The four species of *Babesia* differ with respect to their pathogenicity. The North-African *B. vogeli* strains provoke only mild disease, which usually does not require treatment (like the Australian *B. canis* strains). European *B. canis* strains are more pathogenic than the North-African parasite. In our experiments with the *B. canis* A strain, approximately half of the animals required chemotherapeutic treatment after infection. The South-African *B. rossi* strains are most pathogenic, a feature observed already very early. Using the South-African *B. rossi* strain naive dogs developed progressing disease characterised by exponential parasite growth. In contrast, parasitaemia in dogs infected with European *B. canis* usually is limited. In the latter, congestion appears to be the main pathological feature.

At the moment a vaccine for *Babesia* is prepared from the supernatant of a culture of a strain of *Babesia canis*, as is described in U.S. Pat. No. 4,777,036. However, such a vaccine contains only antigens of the strain of this particular species of *B. canis*. It appears that such a vaccine gives in general little protection against infections with (wild type) *B. canis* (Lepetit, C., Piroplasmose canine et vaccination Pirodog, Doctoral Thesis, Univ. of Nantes, 1988). The author of the thesis gives three possible causes of this failure of protective immunisation:

1. the sensitivity of the dogs with respect to vaccination;
2. the type of immune effector mechanism induced by vaccination;
3. the antigenic diversity of *Babesia*.

Vaccines containing whole, attenuated *Babesia* parasites always harbour the danger that the parasites again become virulent and thus spread the disease instead of curing it. Therefore, the use of subunit vaccines is preferred. Thus there remains the desire for a vaccine which is not infective, which can be easily produced and which yet can give protection against *Babesia canis* infection, preferably against all *Babesia canis* strains.

SUMMARY

It is i.a. an objective of the present invention to provide *Babesia canis* related proteins which are able, each separately, or when combined, to induce protection against *Babesia canis* infection in dogs. It was surprisingly found now, that two such novel proteins exist that are specifically associated with *Babesia canis*: they are not found in the *Babesia* species *B. rossi*.

DETAILED DESCRIPTION

By referring to the novel proteins as associated with *Babesia canis* it is meant that these proteins are found to be present in the *Babesia canis* parasite. It does not mean that the genetic information is found on a chromosome of the parasite. The genetic information for the novel proteins is found in the parasite, but it can be present as extra-chromosomal information.

The novel proteins will be referred to as the 15 kD protein (also Bcvir15) and the 32 kD protein (also Bcvir32). The amino acid sequence of the 15 kD protein is presented in sequence identifier SEQ ID NO: 2. The cDNA encoding this protein has been sequenced and its nucleic acid sequence is shown in sequence identifier SEQ ID NO: 1.

The amino acid sequence of the 32 kD protein is presented in sequence identifier SEQ ID NO: 4. The cDNA encoding this protein has been sequenced and its nucleic acid sequence is shown in sequence identifier SEQ ID NO: 3.

It is well-known in the art, that many different nucleic acid sequences can encode one and the same protein. This phenomenon is commonly known as wobble in the second and especially the third base of each triplet encoding an amino acid. This phenomenon can result in a heterology of about 30% for two different nucleic acid sequences still encoding the same protein. Therefore, two nucleic acid sequences having a sequence homology of about 70% can still encode one and the same protein.

One embodiment of the invention relates to a nucleic acid sequence encoding a 15 kD *Babesia canis* associated protein or an immunogenic fragment of that protein, said protein or immunogenic fragment thereof having at least 80%, preferably 90%, more preferably 95% homology with the amino acid sequence as depicted in SEQ ID NO: 2. Even more preferred is a homology level of 98% or even 100%.

Another embodiment of the invention relates to a nucleic acid sequence encoding a 32 kD *Babesia canis* associated protein or an immunogenic fragment of that protein, said protein or immunogenic fragment thereof having at least 80%, preferably 90%, more preferably 95% homology with the amino acid sequence as depicted in SEQ ID NO: 4. Even more preferred is a homology level of 98% or even 100%.

Needless to say that a nucleic acid sequence encoding a protein according to the invention is understood to apply equally to the RNA encoding the protein and to cDNA and DNA carrying the genetic code of this RNA. As a consequence, where a certain nucleic acid sequence or part thereof is said to have a certain level of homology with e.g. the nucleic acid sequence of SEQ ID NO: 1, this level of homology equally goes for cDNA and the RNA used as a template for making the cDNA, as well as vice versa to (c)DNA and the RNA transcribed from that DNA.

Parts of the said nucleic acid sequences that encode an immunogenic fragment of the proteins to which the invention relates can be very small. Immunogenic fragments of e.g. 4 amino acid length are known. Such immunogenic fragments are encoded by a nucleic acid sequence of 12 nucleotides. Such very short amino acid sequences are however not immunogenic as such: they need to be coupled to a carrier, such as KHL, as known in the art. Longer fragments can be immunogenic as such. Therefore, the parts of the said nucleic acid sequences that encode an immunogenic fragment comprise at least 12 nucleotides. Parts comprising more than 15, more preferably more than 18, 20 25 or even 30 nucleotides are even more preferred in that order of preference.

Since the present invention discloses nucleic acid sequences encoding novel *Babesia canis* associated 15 kD and 32 kD proteins, it is now for the first time possible to obtain these proteins in sufficient quantities. This can e.g. be done by using expression systems to express the genes encoding the proteins.

Therefore, in another embodiment, the invention relates to a cDNA fragment comprising a nucleic acid sequence according to the invention. A cDNA is a copy DNA that has been made, e.g. by reverse transcriptase, of an RNA encoding a protein according to the invention. Such cDNA fragments in their shortest form are a DNA copy of a part of a nucleotide sequence according to the invention. They can however also comprise flanking nucleic acid sequences not naturally present upstream and downstream of the coding sequence.

An essential requirement for the expression of cDNA is an adequate promoter functionally linked to the cDNA, so that the cDNA is under the control of the promoter. It is obvious to those skilled in the art that the choice of a promoter extends to any eukaryotic, prokaryotic or viral promoter capable of directing gene transcription in cells used as host cells for protein expression.

Therefore, another embodiment of the invention relates to a recombinant DNA molecule comprising a cDNA fragment or a nucleic acid sequence according to the invention that is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6).

Functionally linked promoters are promoters that are capable of controlling the transcription of the nucleic acid sequences to which they are linked.

Such a promoter can be a *Babesia* promoter, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of mammalian origin illustrative useful expression control sequences include the SV-40 promoter (Berman, P. W. et al., Science, 222, 524-527, 1983) or the metallothionein promoter (Brinster, R. L., Nature, 296, 39-42, 1982) or a heat shock promoter (Voellmy et al., Proc. Natl. Acad. Sci. USA, 82, 4949-53, 1985).

Bacterial, yeast, fungal, insect and mammalian cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in U.S. NTIS Publication No. U.S. 08/043,109 (Hoffman, S, and Rogers, W.: Public. Date 1 Dec. 1993).

Another embodiment of the invention relates to a Live Recombinant Carrier (LRC) comprising a cDNA fragment according to the invention or a recombinant DNA molecule according to the invention. Such carriers are e.g. bacteria, parasites and viruses. These LRCs are micro-organisms or viruses in which additional genetic information, in this case a nucleic acid sequence encoding the 15 kD or 32 kD protein or an immunogenic fragment thereof according to the invention has been cloned. Animals infected with such LRCs will produce an immunogenic response not only against the immunogens of the carrier, but also against the immunogenic parts of the protein(s) for which the genetic code is additionally cloned into the LRC, e.g. the 15 kD or 32 kD cDNA.

As an example of bacterial LRCs, attenuated *Salmonella* strains known in the art can attractively be used.

Live recombinant carrier parasites have i.a. been described by Vermeulen, A. N. (Int. Journ. Parasitol. 28: 1121-1130 (1998)).

Also, LRC viruses may be used as a way of transporting the nucleic acid sequence into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today-1988. Springer Verlag, New York: pp. 92-99 (1989)).

The technique of in vivo homologous recombination, well-known in the art, can be used to introduce a recombinant nucleic acid sequence into the genome of a bacterium, parasite or virus of choice, capable of inducing expression of the inserted nucleic acid sequence according to the invention in the host animal.

Finally another embodiment of the invention relates to a host cell comprising a nucleic acid sequence according to the invention, a cDNA fragment or a recombinant DNA molecule according to the invention or a live recombinant carrier according to the invention. A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983)), mammalian cells like Hela cells, Chinese Hamster Ovary cells (CHO) or Crandell Feline Kidney-cells, also with appropriate vectors or recombinant viruses.

Another embodiment of the invention relates to the novel *Babesia canis* associated proteins: the 15 kD and 32 kD protein and to immunogenic fragments thereof, according to the invention.

The concept of immunogenic fragments will be defined below.

It will be understood that, for the particular proteins embraced herein, natural variations can exist between the proteins associated with individual *Babesia canis* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain immune reactivity. This explains why *Babesia canis* associated proteins according to the invention, when isolated from different field isolates, may have homology levels of about 80%, while still representing the same protein with the same immunological characteristics, i.e. the capability of inducing an immunological response against a *Babesia canis* infection. Those variations in the amino acid sequence of a certain protein according to the invention that still provide a protein capable of inducing an immune response against infection with *Babesia canis* or at least against the clinical manifestations of the infection are considered as "not essentially influencing the immunogenicity".

Therefore, one form of this embodiment relates i.a. to a *Babesia canis* associated protein that has a molecular weight of 15 kD and comprises an amino acid sequence that is at least 80% homologous to the amino acid sequence as depicted in SEQ ID NO: 2 and to an immunogenic fragment of said protein.

In a preferred form, the embodiment relates to such a *Babesia canis* associated protein that has a sequence homology of at least 85%, preferably 90%, more preferably 95% homology to the amino acid sequence as depicted in SEQ ID NO: 2 and to an immunogenic fragment of such a protein.

Even more preferred is a homology level of 98% or even 100%.

Another embodiment relates i.a. to a *Babesia canis* associated protein that has a molecular weight of 32 kD and comprises an amino acid sequence that is at least 80% homologous to the amino acid sequence as depicted in SEQ ID NO: 4 and to an immunogenic fragment of said protein.

A preferred form of this embodiment relates to such a *Babesia canis* associated protein that has a sequence homology of at least 85%, preferably 90%, more preferably 95% homology to the amino acid sequence as depicted in SEQ ID NO: 4 and to an immunogenic fragment of such a protein.

Even more preferred is a homology level of 98% or even 100%.

The level of protein homology can be determined with the computer program "BLAST 2 SEQUENCES" by selecting sub-program: "BLASTP", that can be found at the United States' National Institutes of Health's National Library of Medicine's National Center for Biotechnology Information world wide web site. A reference for this program is Tatiana A. Tatusova, Thomas L. Madden FEMS Microbiol. Letters 174: 247-250 (1999). Matrix used: "blosum62". Parameters used are the default parameters: Open gap: 11. Extension gap: 1. Gap x_dropoff: 50.

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in the host, i.e. comprises a B- or T-cell epitope. At this moment, a variety of techniques is available to easily identify cDNA fragments encoding antigenic fragments (determinants). The method described by Geysen et al (Patent Application WO 84/03564, Patent Application WO 86/06487, U.S. Pat. No. 4,833,092, Proc. Natl. Acad. Sci. 81: 3998-4002 (1984), J. Imm. Meth. 102, 259-274 (1987)), the so-called PEPSCAN method is an easy to perform, quick and well-established method for the detection of epitopes, the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application NTIS U.S. 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzowsky for HIV-epitopes; The FASEB Journal 5:2412-2418 (1991).

Thus, another embodiment of the invention relates to a vaccine for combating *Babesia canis* infection, that comprises a protein or an immunogenic fragment thereof according to the invention as described above together with a pharmaceutically acceptable carrier.

One way of making a vaccine according to the invention comprises growing the *Babesia canis* parasite, and purification of the 15 kD and 32 kD proteins. This is however a very time-consuming way of making the vaccine. It would thus be less practical to make such vaccines on an industrial scale.

It is one of the merits of the present invention that it provides for the first time the nucleic acid sequences encoding the 15 kD and 32 kD proteins. It is therefore much more convenient to use the expression products of the cDNA encoding these proteins or immunogenic fragments thereof according to the invention in vaccines.

Vaccines based upon the expression products of these cDNAs can easily be made by admixing one or both proteins according to the invention or immunogenic fragments thereof according to the invention with a pharmaceutically acceptable carrier as described below. It is also possible to directly admix a host cell in which one or both proteins according to the invention or immunogenic fragments thereof according to the invention have been expressed and a pharmaceutically acceptable carrier.

Alternatively, a vaccine according to the invention can comprise live recombinant carriers as described above, capable of expressing the proteins according to the invention or immunogenic fragments thereof according to the invention. Such vaccines, e.g. based upon a bacterial (e.g. *Salmonella*) carrier, a parasitic or a viral carrier have the advantage over subunit vaccines that they better mimic the natural way of infection of *Babesia canis*. Moreover, their self-propagation is an advantage since only low amounts of the recombinant carrier are necessary for immunisation.

Thus, still another embodiment relates to a vaccine for combating *Babesia canis* infection, that comprises a live recombinant carrier according to the invention and a pharmaceutically acceptable carrier.

All vaccines described above contribute to active vaccination, i.e. the host's immune system is triggered by one or more proteins according to the invention or immunogenic fragments thereof, to make antibodies against these proteins or fragments or to expand T-cell populations with receptors that can be specifically triggered by epitopes associated with these proteins.

Alternatively, such antibodies can be raised in e.g. rabbits or can be obtained from antibody-producing cell lines as described below. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals. Administered antibodies against *Babesia canis* can in these cases bind directly to the proteins according to the invention and to parasites and cells exposing these proteins. This has the advantage that it decreases or stops *Babesia canis* growth.

Therefore, one other form of this embodiment of the invention relates to a vaccine for combating *Babesia canis* infection comprising antibodies against a *Babesia canis* associated protein according to the invention or an immunogenic fragment of those proteins, and a pharmaceutically acceptable carrier.

Another embodiment relates to a method for the preparation of a vaccine according to the invention that comprises the admixing of antibodies according to the invention and a pharmaceutically acceptable carrier.

Vaccines can also be based upon host cells as described above, that comprise the nucleic acid sequences, cDNA fragments, recombinant DNA molecules or live recombinant carriers according to the invention.

Therefore, another embodiment of the present invention relates to a vaccine for combating *Babesia canis* infection, that comprises a host cell according to the invention and a pharmaceutically acceptable carrier.

An alternative and efficient way of vaccination is direct vaccination with DNA encoding the relevant antigen. Direct vaccination with DNA encoding proteins has been successful for many different proteins (As reviewed in e.g. Donnelly et al., The Immunologist 2: 20-26 (1993)).

This way of vaccination is also attractive for the vaccination of dogs against *Babesia canis* infection.

Therefore, still other forms of this embodiment of the invention relate to a vaccine comprising a nucleic acid sequence according to the invention and a pharmaceutically acceptable carrier, and to a vaccine comprising a cDNA fragment according to the invention and a pharmaceutically acceptable carrier.

Still another form of this embodiment relates to a vaccine comprising a recombinant DNA molecule according to the invention and a pharmaceutically acceptable carrier. DNA vaccines can easily be administered through intradermal application e.g. using a needle-less injector. This way of administration delivers the DNA directly into the cells of the animal to be vaccinated. Amounts of DNA in the microgram range between 1 and 100 µg provide very good results.

In a preferred embodiment, the vaccine according to the present invention comprises an additional antigen derived from a micro-organism or virus pathogenic to dogs, or genetic information encoding such an antigen.

Such dog pathogenic organisms and viruses are preferably selected from the group of *Ehrlichia canis, Babesia gibsoni, vogeli, rossi, Leishmania donovani*-complex, Canine parvovirus, Canine distempervirus, *Leptospira interrogans serovar canicola, icterohaemorrhagiae, pomona, grippotyphosa, bratislava*, Canine hepatitisvirus, Canine parainfluenzavirus, rabies virus, *Hepatozoon canis* and *Borrelia burgdorferi*.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a nucleic acid sequence, a cDNA fragment, a recombinant DNA molecule or a live recombinant carrier according to according to the invention, a host cell according to the invention, or a protein according to the invention or an immunogenic fragment thereof and a pharmaceutically acceptable carrier.

Thus, another embodiment of the present invention relates to a method for the preparation of a vaccine according to the invention, that comprises the admixing of a nucleic acid sequence according to the invention, a cDNA fragment the invention, a recombinant DNA molecule according to the invention, a live recombinant carrier according to the invention or a host cell according to the invention or a protein according to the invention and a pharmaceutically acceptable carrier.

Vaccines according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers, muramyldipeptides, saponins such as QUILL A®, mineral oil e.g. BAYOL® or MARKOL®, vegetable oil, and CARBOPOL® (a homopolymer), or DILU-VAC® Forte.

The vaccine may also comprise a so-called "vehicle". A vehicle is a compound to which the protein adheres, without being covalently bound to it. Often used vehicle compounds are e.g. aluminium hydroxide, -phosphate or -oxide, silica, Kaolin, and Bentonite.

A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g. Span or Tween.

Often, the vaccine is mixed with stabilisers, e.g. to protect degradation-prone proteins from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

It goes without saying, that other ways of adjuvating, adding vehicle compounds or diluents, emulsifying or stabilising a protein are also embodied in the present invention. Thus, a preferred form of this embodiment relates to a vaccine for combating Babesia canis infections according to the invention that comprises an adjuvant.

Vaccines according to the invention can very suitably be administered in amounts ranging between 1 and 100 micrograms, although smaller doses can in principle be used. A dose exceeding 100 micrograms will, although immunologically very suitable, be less attractive for commercial reasons.

Vaccines based upon live attenuated recombinant carriers, such as the LRC-viruses, parasites and bacteria described above can be administered in much lower doses, because they multiply themselves during the infection. Therefore, suitable amounts would range between $10^3$ and $10^9$ CFU/PFU for respectively bacteria, parasites and viruses.

Many ways of administration can be applied. Systemic application is a suitable way of administration, e.g. by intramuscular application of the vaccine. If this route is followed, standard procedures known in the art for systemic application are well-suited. Intradermal, sub-cutaneous and intracutaneous ways of administration are also attractive. Still another embodiment of the present invention relates to a *Babesia canis* associated protein according to the invention for use in a vaccine.

Still another embodiment of the present invention relates to the use of a *Babesia canis* associated protein according to the invention for the manufacturing of a vaccine for combating *Babesia canis* infections.

From a point of view of protection against disease, a quick and correct diagnosis of *Babesia canis* infection is important.

Therefore it is another objective of this invention to provide diagnostic tools suitable for the detection of *Babesia canis* infection.

A diagnostic test for the detection of *Babesia canis* is e.g. based upon the reaction of RNA isolated from the animal to be tested, with specific probes or it is e.g. a RT-PCR test based upon the coding sequences for the 15 kD or the 32 kD proteins or based upon nucleic acid sequences that are complementary to those coding sequences. If nucleic acid molecules specific for the *Babesia canis* associated proteins according to the invention are present in the animal, these will e.g. specifically bind to specific PCR-primers and will subsequently become amplified in RT-PCR-reaction. The PCR-reaction product can then easily be detected in DNA gel electrophoresis. RT-PCR reactions are well-known in the art (see reference below). The nucleic acid molecules can most easily be isolated from (the parasites present in) erythrocytes of the animal to be tested. Standard PCR-textbooks give methods for determining the length of the primers for selective PCR-reactions with nucleic acid molecules specific for the *Babesia canis* associated proteins according to the invention. Primers with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in (Dieffenbach & Dreksler; PCR primers, a laboratory manual. ISBN 0-87969-447-5 (1995)).

Nucleic acid molecules encoding a *Babesia canis* associated protein or parts of those nucleic acid molecules having a length of at least 12, preferably 15, more preferably 18, even more preferably 20, 22, 25, 30, 35 or 40 nucleotides in that order of preference, wherein the nucleic acid molecules or parts hereof have at least 70% homology with the nucleic acid sequence as depicted in SEQ ID NO: 1 or 3 or a nucleic acid sequence that is complementory to nucleic acid sequence as depicted in SEQ ID NO: 1 or 3 are therefore also part of the invention. Such nucleic acid molecules can e.g. be used as primers in (RT-)PCR-reactions in order to enhance the amount of nucleic acid that encodes the proteins according to the invention. This allows the quick amplification of specific nucleotide sequences for use as a diagnostic tool for e.g. the detection of *Babesia* in tissue as indicated above.

The level of nucleotide homology can be determined with the computer program "BLAST 2 SEQUENCES" by selecting sub-program: "BLASTN" that can be found at the United States' National Institutes of Health's National Library of Medicine's National Center for Biotechnology Information world wide web site. A reference for this program is Tatiana A. Tatusova, Thomas L. Madden FEMS Microbiol. Letters 174: 247-250 (1999). Parameters used are the default parameters: Reward for a match: +1. Penalty for a mismatch: −2. Open gap: 5. Extension gap: 2. Gap x_dropoff: 50.

Another nuclei acid-based test is based upon growth of parasite material obtained from erythrocytes, followed by classical RNA purification followed by cDNA synthesis and/or classical hybridisation with radioactively or colour labelled 15 kD or 32 kD protein-specific cDNA-fragments.

Both PCR-reactions and hybridisation reactions are well-known in the art and are i.a. described in Maniatis/Sambrook (Sambrook, J. et al. Molecular cloning: a laboratory manual. ISBN 0-87969-309-6).

Thus, another embodiment of the invention relates to a diagnostic test for the detection of *Babesia canis* associated RNA characterised in that the test comprises a nucleic acid sequence that is at least 70% homologous to the nucleic acid sequence as depicted in SEQ ID NO: 1 or 3 or a nucleotide sequence that is complementary to that nucleic acid sequence, or a fragment thereof having a length of at least 12, preferably 15, more preferably 18 nucleotides.

A diagnostic test for the detection of antibodies against the *Babesia canis* associated proteins in e.g. sera, tissue or body fluids can be e.g. a simple standard ELISA-test in which 15 kD or 32 kD protein or antigenic fragments thereof according to the invention are coated to the wall of the wells of an ELISA-plate. A method for the detection of such antibodies is e.g. incubation of 15 kD or 32 kD protein or antigenic fragments thereof with serum from mammals to be tested, followed by e.g. incubation with a labelled antibody against the relevant mammalian antibody. A colour reaction can then reveal the presence or absence of antibodies against *Babesia canis* associated protein. Another example of a diagnostic test system is e.g. the incubation of a Western blot comprising the 15 kD or 32 kD protein or an antigenic fragment thereof according to the invention, with serum of mammals to be tested, followed by analysis of the blot.

Thus, another embodiment of the present invention relates to a diagnostic test for the detection of antibodies against *Babesia canis* associated antigenic material, characterised in that the test comprises a protein or an immunogenic fragment thereof according to the invention.

A diagnostic test based upon the detection of antigenic material of the specific 15 kD and 32 kD proteins amongst *Babesia canis* antigens and therefore suitable for the detection of *Babesia canis* infection can e.g. also be a standard sandwich-ELISA test. In one example of such a test the walls of the wells of an ELISA plate are coated with antibodies directed against the 15 kD or 32 kD protein or immunogenic fragments thereof. After incubation with the material to be tested, labelled anti-Babesia canis antibodies are added to the wells. A colour reaction then reveals the presence of antigenic material from *Babesia canis*.

Therefore, still another embodiment of the present invention relates to a diagnostic test for the detection of *Babesia canis* associated antigenic material, characterised in that said test comprises antibodies against a protein or an immunogenic fragment thereof according to the invention.

The proteins or immunogenic fragments thereof according to the invention expressed as described above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. Immunochemical Methods in Cell and Molecular Biology, Academic Press, London, 1987).

Monoclonal antibodies, reactive against the protein according to the invention (or variants or fragments thereof) according to the present invention, can be prepared by immunising inbred mice by techniques also known in the art (Kohler and Milstein, Nature, 256, 495-497, 1975).

Still another embodiment of the invention relates to methods for the detection of antigenic material from *Babesia canis* in which the method comprises the incubation of serum, tissue of body fluids with antibodies against the 15 kD or the 32 kD protein or an antigenic fragment thereof according to the invention.

EXAMPLES

Example 1

Molecular Characterisation of BCVIR cDNA

Growth of *Babesia canis*

Isolates of *Babesia canis* (isolate A and B) were obtained from dogs naturally infected in France. They were maintained in in vitro culture according to Schetters et al. (1997, *Parasitology*, 115, 485-493).

cDNA Library Construction, Immunological Screening and Isolation of Plasmid DNA.

A cDNA library from *Babesia canis* (isolate A) was constructed with the ZAP Express™ cDNA Gigapack® II Gold Cloning kit (Stratagene) as it was described for *B. rossi* in Carret et al. (1999, *Eur. J. Biochem.*, 265, 1015-1021). The library was screened as described in Carret et al. (1999, *Eur. J. Biochem.*, 265, 1015-1021) using the anti-GST60.1 (depleted of anti-*E. coli* antibodies), a polyclonal antibody directed against one member of the *Plasmodium falciparum* Pf60 multigene family (Carcy et al., 1994, *Mol. Biochem. Parasitol.* 68: 221-233), at a 1:100 dilution. Positive clones were visualised using goat anti-rabbit IgG conjugated to peroxidase (Sigma) at a 1:500 dilution, using 4-chloro-1-naphtol as chromogen (Sigma). They were purified and the pBK-CMV plasmids carrying the BCVIR cDNA were prepared as described in Carret et al. (1999, *Eur. J. Biochem.*, 265, 1015-1021).

DNA Sequencing

Nucleotid sequence was performed using the dideoxy chain termination method from alkali-denaturated double-strand templates according to Sanger et al. (1977, *Proc. Natl. Acad. Sci. USA* 74 (12):5463-5467) by Genome Express S.A (Zone Astec, Grenoble, France) on both strands of the selected plasmids using T3, T7 universal primers and oligonucleotides derived from established sequence of each strand.

Cloning of the 5' End of the BCVIR cDNA

In order to obtain the full-length BCVIR cDNA sequence, the missing 5' end was obtained as follows: the cDNA library was used as a DNA template for a PCR experiment using the T3 sense universal primer derived from the vector sequence (located 70 bp upstream of the EcoRI cloning site) and an antisense primer P2 (5'-ATGAGTCTATTGACTCCTTG-3' (SEQ. ID. NO.: 15)) derived from the BCVR cDNA sequence (nucleotide position 476-496 downstream of the EcoRI cloning site in the complete sequence of the cDNA, see FIG. 1 and FIG. 2). The PCR was performed as described below (§ PCR amplification) using 1 µl of the cDNA library ($10^5$ phages) as DNA template. The highest resulting PCR fragment (with a size of around 550 bp) was gel-extracted using gel extraction spin columns (Genomed), cloned in pGEM®-T vector using the pGEM®-T vector System II kit under the recommendations of Promega and sequenced on both strands as described behind, using T7 and SP6 universal primers (Genome Express).

PCR Amplification

Amplifications were performed in a PTC-100™ Programmable Thermal Controller (MJ Research, INC.) as described in Carret et al. (1999, *J. Eukaryot. Microbiol.*, 46(3), 298-

303) with the following conditions: 3 min. at 94° C., 30 cycles of 1 min. at 94° C., 1 min. at 55° C. and 1 min. at 72° C., and then 5 min. at 72° C. Primers P1 (sense 5'-GACGTTTGAT-GTGATGAGGGAAGC-3' (SEQ. ID. NO.: 12)), P5 (sense 5'-AGGGAGCTGTCACGGAAGATT-3' (SEQ. ID. NO.: 13)), P2 (antisense) and P15.2 (antisense 5'-AATGACAT-ACTCACAGGAAGC-3' (SEQ. ID. NO.: 14)) were all derived from the BCVIR cDNA sequence (their respective position is indicated on the FIG. 1) and commonly used for the molecular analysis of this sequence.

Genomic DNA Analysis of the BCVIR cDNA Sequence:

Genomic DNA extraction from *Babesia canis* cultures and Southern blot experiments were performed using standard procedures described in Maniatis/Sambrook (Sambrook J. et al., Molecular cloning: a laboratory manual. ISBN 0-87969-309-6).

The probes were obtained by performing PCR with the combinations of primers P1/P15.2 or P1/P2 using the pBK-CMV plasmid carrying the BCVIR cDNA as DNA template and they were labelled using Nick Translation kit under the recommendations of the manufacturer (Boehringer Mannheim). These probes were also tested on chromosomes of *B. canis* separated in 0.7% agarose (ICN) by pulse field gel electrophoresis (PFGE) and transferred onto Nylon membranes.

As control, hybridisation experiments were performed with a probe derived from the Bcc12D3 cDNA of *B. canis* A on the same membranes that were hybridized with probes derived from the BCVIR cDNA sequence. Dehybridisation was performed as recommended by Amersham Pharmacia Biotech.

RNA Analysis of the BCVIR cDNA Sequence:

Total RNA was extracted using the RNAgents® Total RNA Isolation System according Promega and was used as starting material for RT/PCR and Northern experiments.

RT-PCR. RT-PCR was performed using the two-step protocol of the Enhanced Avian RT-PCR kit as described by the manufacturer (Sigma). Briefly, the first step (retrotranscription) was performed for 50 min. at 42° C. using 250 pg of total RNA as template and 1 µM of specific cDNA primer (sense P1, sense P5 (5'-AGGGAGCTGTCACGGAAGATT-3' (SEQ. ID. NO.: 13)) or antisense P15.2), and the second step was performed at an annealing temperature of 50° C. as described above (§PCR amplification), using one fifth of the first step reaction as a template. As controls, the first step was also performed without eAMV-RT for each primer tested for DNA contamination, and the experiments were also performed with specific primers (sense Bcc12D3.1 and antisense Bcc12D3.2) derived from the Bcc12D3 cDNA of *B. canis* A.

Northern Blotting. For Northern blot experiments, total RNA was electrophoresed through gel containing formaldehyde and transferred to Nylon membrane as described in Maniatis/Sambrook (Sambrook J. et al., Molecular cloning: a laboratory manual. ISBN 0-87969-309-6). Hybridisation was performed with a probe derived from a P1/P2 PCR fragment amplified on the BCVIR cDNA sequence and labelled with digoxigenin (DIG)-dUTP according the DIG High Prime DNA labelling kit (Boehringer Mannheim). Total RNA samples depleted in mRNA were also used for hybridisation experiments and mRNA depletion was performed using PolyA Tract mRNA Isolation Systems® III kit (Promega).

Results:

Isolation and sequence of the BCVIR cDNA. Immunoscreening of a cDNA library of *B. canis* (isolate A), using the anti-GST60.1 antiserum directed against one member of the Pf60 multigene family of *P. falciparum* (Carcy et al., 1994, Mol. Biochem. Parasitol. 68: 221-233) allowed to isolate and sequence the BCVIR cDNA.

The complete nucleotide sequence of BCVIR cDNA contained 1135 nucleotides (between EcoRI to XhoI cloning restriction sites) with a poly(A)$_{22}$ tail (FIG. 1A and FIG. 2). An interesting feature of this cDNA is that two overlapping open reading frames (ORF) are predicted (FIG. 1A): ORF1 between nucleotide 75 (ATG, initiation codon for Methionine) and 500 (TAA, stop codon) and ORF2 between nucleotides 448 (ATT codon for Isoleucine) and 933 (TGA, stop codon). These two ORF are overlapped by 52 nucleotides (position 448-500) and are +1 shifted (FIG. 1A).

ORF1 encodes a predicted polypeptide of 141 residues (designated Bcvir15) starting by a methionine with an expected molecular mass of 15.7 kDa and an iso-electric point of 10.9 (FIG. 2). ORF2 does not contain a consensus translation initiation sequence and started by Ile (FIG. 1A). It encodes a predicted polypeptide of 133 residues with an expected molecular mass of 15.2 kDa. Due to the +1 shift between ORF1 and ORF2, these two ORFs present different amino acid sequences in the overlapping region (FIG. 1B). Sequence analysis of the overlap region of BCVIR cDNA suggested that such a +1 ribosomal frame shift in that region could produced an ORF1-ORF2 fusion protein of 285 residues (designated Bcvir32), resulting from the translation of a 859 nucleotides sequence (FIG. 3). Bcvir32 would have predicted molecular mass of 32.3 kDa and an iso-electric point of 10.5.

DNA analysis: The presence of BCVIR cDNA sequence in the genome of *B. canis* (isolates A and B) was analysed by PCR and hybridisation experiments both on DNA (Southern blot) or chromosomes (PFGE) from these isolates.

PCR experiments. These were performed using 3 combinations of specific primers from the BCVIR cDNA sequence: P1/P2 and P5/P2 covering the ORF1 (FIGS. 4A and 4B, respectively), and P5/P15.2 covering the ORF2 and the overlapping region between these two ORF of the cDNA (FIG. 4C). As controls, these combinations of primers allowed to amplify DNA fragment of around 360, 160 and 630 bp on the cDNA BCVIR carried by the pBK-CMV plasmid (FIG. 4A-C, lanes 5) and were negative on genomic DNA prepared from uninfected dogs (FIG. 4A-C, lanes 4). These combinations of primers were unable to amplify genomic DNA fragments when they were tested on genomic DNA from the isolates A and B of *B. canis* (FIG. 4, lanes 1 and 2, respectively) whereas, as control for the DNA preparations, specific primers derived from the Bcc12D3 cDNA of *B. canis* were able to specifically amplify the expected 1200 bp genomic DNA fragment on these preparations (FIG. 4D, lane 1 and 2, respectively). Moreover, primers from the BCVIR cDNA sequence were negative in PCR on genomic DNA from the isolate F of *B. rossi* as were those derived from the Bcc12D3 cDNA (FIG. 4, lanes 3).

Hybridisation experiments. hybridisation with probes synthesised using the PCR fragments P1/P2 and P1/P15.2 from the BCVIR cDNA sequence, were performed on genomic DNA of isolates A and B of *B. canis* and isolate F of *B. rossi*, either digested by various restriction enzymes (Southern blot)

or on chromosomes (separated by PFGE). Whatever the hybridisation experiment performed, none of these probes allowed to detect the BCVIR sequence on genomic DNA of *B. canis*, whereas following de-hybridisation of these probes from the membranes, a probe derived from the Bcc12D3 cDNA sequence was able to detect its sequence on genomic DNA of *B. canis* (data not shown).

RNA analysis. Analysis of the BCVIR cDNA sequence was performed by RT-PCR (FIG. 5, A-C) and hybridisation experiments (Northern blot) (FIG. 6) using total RNA extracted from the isolate A of *B. canis*.

RT-PCR experiment. For the RT-PCR analysis of BCVIR sequence, analysis of the Bcc12D3 cDNA sequence was used as control (FIGS. 5D and 5E). As expected for this control, the 1200 bp DNA fragment from Bcc12D3 was amplified by PCR with the combination of primers Bcc12D3.1/Bcc12D3.2 when the first retrotranscription step was performed with antisense primer Bcc12D3.2 (FIG. 5E, lane 5), but not when it was performed with the sense primer Bcc12D3.1 (FIG. 5D, lane 4). For the analysis of BCVIR sequence, the expected 630 bp DNA fragment was amplified by PCR with the combination of primers P5/P15.2 PCR when the first step of retrotranscription was performed with the antisense primer P15.2 (FIG. 5C, lane 3). However and unexpectedly, this DNA fragment of 630 bp was also amplified by PCR with this P5/P15.2 combination of primers when the first step of retrotranscription was performed with the sense primer P5 (FIG. 5B, lane 2). Identically, a unexpected 360 bp DNA fragment was amplified by PCR with the P1/P2 combination of primers when the first step of retrotranscription was performed with the sense primer P1 (FIG. 5A, lane 1). The same experiments performed by omitting the e-AMV Retrotranscriptase enzyme in the retrotranscription steps did not allow to amplify DNA fragment by PCR with these combination of primers (FIG. 5, lanes 1'-5'), demonstrating that the 360 and 630 bp DNA fragment amplified using the sense primers P1 or P5 in the retrotranscription step were not from genomic DNA origin, as previously observed (§ DNA analysis). Moreover, their sequencing and their hybridisation with a probe derived from the entire BCVIR cDNA sequence (FIG. 5, II) certified their specificity.

Northern blot experiment. hybridisation performed onto total RNA extracted from *B. canis* (isolate A) with a probe corresponding to the ORF1 sequence of BCVIR cDNA allowed to detect three different RNA bands: a strong one of around 1400 bases length and two faint ones at around 1200 and 2800 bases length (FIG. 6, lane 2). When hybridisation was performed with the same amount of starting total RNA but depleted in mRNA, the 1200 bases band disappeared (FIG. 6, lane 3), indicating that this RNA band is a mRNA, in agreement with the size of the cDNA. It confirms also that the BCVIR cDNA sequence is carried by non messenger RNA (the 1400 and 2800 bases length bands), in agreement with the results obtained by RT-PCR when the retrotranscription step was performed with sense primer.

No signal was found when hybridised with the BCVIR cDNA sequence onto total RNA from *B. rossi* (FIG. 6, lane 4) or the bovine species *B. divergens* (FIG. 6, lane 1).

Conclusion: The molecular characterisation of the BCVIR cDNA sequence indicates that it is not from *B. canis* genomic DNA origin. It demonstrates that it is carried by a mRNA, but also by a non messenger RNA of 1.4 kb and 3 kb. It demonstrates also that the sequence from this cDNA is specifically found in the European isolates of *B. canis*, not in *Babesia rossi*.

Example 2

Biochemical Characterisation of Proteins Encoded by the BCVIR cDNA Sequence

Expression and Purification of GST-ORF1 and GST-ORF2 Recombinant Proteins in *E. coli*.

In order to express the products encoded by ORF1 and ORF2 from the BCVIR cDNA as recombinant proteins, and to produce specific antisera against them, the two ORFs were subcloned in the EcoRI/XhoI cut dephosphorylated pGEX-4T3 vector (Amersham Pharmacia Biotech) in frame with the glutathione-S-transferase (GST).

In order to produce Bcvir15 protein encoded by ORF1 (aa $M^1$-$I^{141}$, FIG. 2), the EcoRI/XhoI fragment containing the 1041 bp cDNA sequence (missing the 5' end of BCVIR cDNA) was excised from the pBK-CMV recombinant plasmid and subcloned into the vector. In order to obtain an antiserum specifically directed against the amino acid sequence deduced from the ORF2 sequence (aa sequence $N^{154}$-$C^{285}$, FIG. 3), i.e. excluding the 52 bp overlapping region between the two ORF (nucleotide position 448-500 in FIG. 1), an EcoRI restriction site was created in the ORF2 sequence by a PCR experiment. Thus, the 1041 bp BCVIR cDNA sequence carried by the pBK-CMV plasmid was used as template DNA for the PCR experiment with the sense primer $P_{Eco}$ (5'-ATGAGGAATTCGAACCGACTA-3' (SEQ ID NO.: 10); located at nucleotide position 529-549 on the complete BCVIR cDNA sequence, FIG. 1 and FIG. 2) and the antisense T7 universal primer derived from the vector sequence (located 75 bp downstream of the XhoI cloning site). The amplified fragment was cloned in pGEM®-T vector using the pGEM®-T vector System II kit under the recommendations of Promega. An EcoRI/XhoI fragment containing an around 600 bp DNA from ORF2 was released from the recombinant plasmid and then subcloned into the vector. For both clonings, transformation with the ligation mixtures were performed into the *E. coli* BL21 cells and positive clones were selected using PCR with the specific primers from the BCVIR cDNA sequence.

Expression and purification of the recombinant GST-Bcvir15 protein and of a non recombinant GST from the pGEX-4T3 vector was performed according Smith and Johnson (1988, *Gene*, 67(1):31-40). However, the GST-ORF2 was unpurifiable using this standard procedure, because it aggregates in inclusion bodies. Thus, inclusion bodies were firstly isolated from total cell extract according the protocol of Nagai & Thogersen (1987, In *Methods in enzymology* (ed. R. Wu and L. Grossman), 153, 461-481). They were then dissociated and loaded on a 12% SDS-PAGE (Laemmli UK, 1974, *Nature* (London), 287:680-685). Lastly, the recombinant GST-ORF2 was electro-eluted from the gel and was used to immunise a rabbit as described below.

Production of antibodies directed against GST-ORF1 and GST-ORF2 proteins. Polyclonal antisera. Polyclonal antiserum raised against GST-ORF1 was produced both in mice and in a rabbit, and a polyclonal antiserum raised against GST-ORF2 was produced in a rabbit according E. Harlow & D. Lane (Antibodies: a laboratory manual. ISBN 2-907516-15-9). Rabbits (New Zealand White) were immunised with 50 µg of purified GST recombinant proteins emulsified in Freund's Complete Adjuvant (FCA) (Sigma) subcutaneously for the first injection, and by intramuscular injections for the two subsequent ones using Freund's Incomplete Adjuvant (FIA) (Sigma). Balb/C mice were intraperitoneally immunised with 15 μg of GST-ORF1 emulsified in FCA for the first injection and in FIA for the two subsequent ones. Injection of the animals was performed at 3-week intervals and the bleedings were done 8 days before each immunisation.

Production and screening of monoclonal antibodies. 48 h prior to fusion of splenocytes from the mice immunised with the recombinant GST-ORF1 with X-63 Ag8-653 myeloma cells, a last injection of 15 μg of GST-ORF1 was performed. The fusion process and cloning by limiting dilution for the isolation of monoclonal antibodies were performed according to Brown et al. (1979, J. immunol. Methods, 31:201-209). Hybridoma supernatants were screened by indirect immunofluorescence assay as described below.

Immunological Methods:

Immunoblotting. Immunoblotting was performed with purified *B. canis* merozoites prepared as follows: parasitized erythrocytes from in vitro culture (20% of parasitaemia) were extensively washed with sterile RPMI 1640 medium (Life Technologies). The pellet was lysed with α-hemolysin from *S. aureus* (Sigma) at a final concentration of 36 U/ml during 30 min. at 37° C. Free merozoites and remaining unlysed cells were pelleted by centrifugation (3500 g, 30 min.) and the supernantant was discarded. The pellet was washed one time with TBS, resuspended in 2 ml of TBS and the merozoites were purified by centrifugation (3500 g, 30 min.) on a gradient of saccharose formed by a lower layer of 1.09 density and a upper layer of 1.02 density. Free merozoites were harvested at the interface, they were pelleted by centrifugation (15000 g, 10 min.) and washed 3 times with TBS. They were then processed for electrophoresis and the proteins were separated on a 15% SDS-PAGE. Immunoblotting was performed as described for *B. divergens* in Carcy et al. (1991, *Biol. Cell*, 72, 93-102) using a 1:100 dilution for the polyclonal antisera directed against GST-ORF1 and GST-ORF2 proteins.

Indirect immunofluorescence assays (IFA). IFA and double IFA were performed on *B. canis* parasitized erythrocytes (5% of parasitaemia) as described for *P. falciparum* in Grellier et al. (1994, *Biol. Cell*, 82, 129-138) using a 1:200 dilution for the polyclonal antisera directed against GST-ORF1 and GST-ORF2 proteins. For double IFA, the slides were first incubated with the anti-GST-ORF2 rabbit antiserum and then with mouse polyclonal or monoclonal antibodies directed against the GST-ORF1. Slides were mounted with Citifluor solution (Citifluor Ltd, London, UK) for limiting extinction fluorescence and the fluorescence was detected using a fluorescence microscope (Axioscope, Zeiss).

[$^{35}$S]-methionine radiolabelling of *B. canis* culture and immunoprecipitation. [$^{35}$S]-methionine radiolabelling of in vitro cultures of *B. canis* with 50 μCi/ml (1200 Ci/mmol, Amersham-Pharmacia Biotech) and a 5% starting parasitaemia, and immunoprecipitation assays were performed as described for *B. divergens* in Carcy et al. (1991, *Biol. Cell*, 72, 93-102).

Protein phase separation by TX-114 treatment. The proteins of *B. canis* were phase separated in Triton X-114 (Sigma) as described for *B. divergens* in Precigout et al. (1991, *Infect. Immun.*, 59(8), 2799-2805) using 200 μl of [$^{35}$S]-methionine radiolabeled parasitized red blood cells (20% of parasitaemia) as starting material.

In Vitro translation of the BCVIR cDNA sequence. The ability of the BCVIR cDNA to direct frame shifting was examined in an in vitro-translation system. In vitro-translation products were synthesised using the TNT® Quick Coupled Transcription/Translation System (Promega) with a PCR DNA fragment containing the entire BCVIR cDNA sequence, a Kozacks sequence and a T7 promoting sequence at its 5' end for the in vitro translation. In order to amplify such a DNA fragment, the PCR was performed on the pBK-CMV plasmid carrying the incomplete 1041 bp BCVIR cDNA as DNA template using the two following primers: a 90 mer sense oligonucleotide (primer P0: 5'-GGATCCTAATAC-GACTCACTATAGGGAGACCACCATG-GAGTCGACATCAACAG ACCAACTTTGTTGC-CGAGAACCGTCCCACCTTTGG-3' (SEQ. ID. NO.: 16)), containing a Kozacks and a T7 promoting sequences but also the missing 5' end of the entire BCVIR cDNA sequence containing the starting ATG codon of the ORF1 (bolded in the primer sequence; nucleotide position 75-130 on the complete cDNA sequence; see FIG. 1 and FIG. 2), and the antisense primer P15.2 from the BCVIR cDNA sequence. The PCR was performed using 100 ng of the circular recombinant pBK-CMV plasmid and the following conditions of amplification were used: 1 cycle of 3 min. at 94° C.; 5 cycles of 1 min. at 94° C., 1 min. at 37° C. and 1 min. at 72° C.; 25 cycles of 1 min. at 94° C., 1 min. at 50° C. and 1 min. at 72° C. The PCR products were gel extracted twice to ensure their purity and resuspended in nuclease free water at a concentration of 100 ng/μl. Then, they were added into a reticulocyte lysate to be translated using the TNT® Quick Coupled Transcription/ Translation System as described by the manufacturer (Promega). As control, the same experiment was performed by omitting the PCR fragment in the reaction. The total radiolabeled translated products (5 μl of the reaction) and immunoprecipitated products (from 20 μl of the reaction) with the anti-GST-ORF1 or the anti-GST-ORF2 or the anti-GST antisera and the pre-immune rabbit serum were separated on a 15% SDS-PAGE.

Results:

Purification of GST-ORF1 and GST-ORF2. In order to produce polyclonal antibodies specifically directed against polypeptide encoded by ORF1 or ORF2, the 141 residues ($^1$M-$^{141}$I) of ORF1 (encoded from $^{75}$ATG to the stop codon TAA$^{500}$) (FIG. 2) and 132 residues ($^{154}$N-$^{285}$C) of the ORF2 (encoded from nucleotide position $^{533}$ATT to the stop codon TGA$^{933}$) (FIG. 3) were cloned in the pGEX-4T3 vector in frame with the GST sequence. Overexpression of the GST-ORF1 and GST-ORF2 were performed in the BL21 *E. coli* strain (FIG. 7). Expression studies demonstrated that *E. coli* cultures containing the recombinant pGEX 4T3-ORF1 expressed, after IPTG induction, the GST-ORF1 protein as a soluble protein in the lysate of sonicated bacteria (FIG. 7A, lane 1). After elution, the soluble GST-ORF1 was purified and it presented the expected molecular mass of 40 kDa (FIG. 7A, lane 2). In contrast, the GST-ORF2 was insoluble in *E. coli* cultures containing the recombinant pGEX 4T3-ORF2 and the recombinant protein, with a molecular mass of 39 kDa, was mainly found in inclusion bodies (FIG. 7B, lane 5). In order to immunise a rabbit with the purified GST-ORF2, it was gel excised from an extract of purified inclusions bodies separated on 12% SDS/PAGE (FIG. 7B, lane 4).

As control, a GST was purified after IPTG induction of an *E. coli* culture containing the native pGEX 4T3 (FIG. 7B, lane 3).

Immunological studies: Polyclonal antisera, raised against GST-ORF1 or GST-ORF2 or GST, were produced by immunising mice and rabbits in order to perform immunological studies of the cDNA encoded polypeptides. Two monoclonal antibodies directed against GST-ORF1 were also tested.

Immunoprecipitation experiments. in a first experiment, they were performed both on the total (FIG. 8A) and exoantigens (FIG. 8B) radiolabelled fractions of *B. canis* cultures (isolate A). In the total antigen fraction, the anti-GST-ORF1 strongly recognises a major product of 15 kDa (Bcvir15, indicated by an asterisk) and a minor product of around 32 kDa (putative Bcvir32, indicated by an arrow) (FIG. 8A, lane 3). In the exoantigen fraction, only the minor product of around 32 kDa was detected faintly (FIG. 8B, lane 3). The anti-GST-ORF2 was found not reactive against a 32 kD protein on the total or exoantigen fractions (FIG. 8, lanes 4). Pre-immune rabbit and anti-GST antisera were not reactive on the antigens recognised with the anti-GST-ORF1 antiserum (FIG. 8, lanes 1 and 2, respectively). In a second experiment, the hydrophylic and hydrophobic fractions of *B. canis* (isolate A) antigens, obtained following TX-114 treatment, were analysed by immunoprecipitation with the anti-GST-ORF1 (FIG. 9). It allowed to detect the 15 kDa protein is the hydrophilic fraction (FIG. 9A, lane 2, indicated by an asterisk) and no reactivity was observed in the hydrophobic fraction (FIG. 9B, lane 2). As control, no reactivity was observed against the 15 kDa protein when the immunoprecipitation was performed with the pre-immune rabbit serum (FIG. 9, lanes 1). MAb directed against GST-ORF1 were not reactive in immunoprecipitation experiments.

Western blot. Western blots were performed with purified merozoites from the isolate A of *B. canis*. The anti-GST-ORF1 specifically recognised the 15 kDa protein (FIG. 10A, lane 2, indicated by an asterisk) but, in contrast to immunoprecipitation experiments, it did not recognise the minor 32 kDa product. However, the anti-GST-ORF2, which recognised different proteins in Western blot experiment, was able to detect such a 32 kDa antigen (FIG. 10B, lane 2, indicated by an arrow). No protein of around 15 kDa (which could correspond to predicted 15.2 kDa polypeptide of the ORF2) was recognised by the anti-GST-ORF2. As controls, pre-immune rabbit serum from each antiserum were not reactive in western blot (FIG. 10, lanes 1). MAb directed against GST-ORF1 were not reactive in Western blot.

Immunofluorescence assays. IFA tests were performed on fixed blood smears from in vitro cultures of the isolates A of *B. canis* (FIG. 11) with the anti-GST-ORF1 and the anti-GST-ORF2. The fluorescence obtained with the polyclonal rabbit anti-GST-ORF1 was associated with numerous intraparasitic vesicles, dispersed through all the parasite cytoplasm but excluding the parasite's nucleus (FIG. 11, picture A). The same pattern of immunofluorescence was observed with the mAb directed against GST-ORF1. Moreover, a double IFA performed with the mAb directed against GST-ORF1 and the polyclonal rabbit anti-GST-ORF2 indicated that antigens recognised by anti-GST-ORF2 (FIG. 11, picture B) co-localised with those recognised by the anti-GST-ORF1. As controls, anti-GST and pre-immune rabbit antiserum were not reactive in IFA tests. The same profile of fluorescence was observed when the IFA tests were performed on infected erythrocytes from the isolate B of *B. canis* (data not shown).

In vitro translation of the BCVIR cDNA. An in vitro translation of the entire BCVIR cDNA sequence was performed in reticulocyte lysate in order to analyse, by immunoprecipitation experiments, its products of expression (FIG. 12, lanes 3-4). Analysis of total expression products revealed that a major 15 kDa protein was expressed when the experiment was performed with the cDNA (FIG. 12, lane 4; indicated by an asterisk) but not when it was performed by omitting the cDNA as control (FIG. 12, lane 1). This major 15 kDa protein was specifically immunoprecipitated by the anti-GST-ORF1 but also a minor protein of around 32 kDa (FIG. 12, lane 3; indicated by an arrow). As controls, the pre-immune rabbit serum and the anti-GST antiserum were not reactive on these products (data not shown). Thus, it suggests that such a minor 32 kDa product could result from the predicted +1 frame shift mechanism. As was the case for immunoprecipitation assays previously described, the anti-GST-ORF2 was not reactive on this minor product (data not shown).

Conclusion: The anti-GST-ORF1 antiserum is able to detect two proteins, a hydrophilic major one of 15 kDa and a minor one of 32 kDa, the last one being detected in the supernatant of in vitro culture of *B. canis*. The anti-GST-ORF2 antiserum was also able to detect a 32 kDa protein, but was unable to detect a 15 kDa product. It indicates that the ORF1 of the BCVIR cDNA encodes for a 15 kDa protein (predicted 15.7 kDa product, designated Bcvir15) and that ORF2 is unable to synthesise the predicted 15.2 kDa product. Moreover, the detection of a 32 kDa protein commonly recognised by anti-GST-ORF1 and anti-GST-ORF2 antisera, suggest that it could correspond to the predicted 32.3 kDa product resulting from a +1 frame shift mechanism and allowing to produce a fused ORF1-ORF2 protein (designated Bcvir32). The in vitro translation of the BCVIR cDNA sequence indicated that such a mechanism might occur in the cDNA sequence. The low level of expression of a 32 kDa protein in comparison with the high expression level of Bcvir15 protein is in agreement with such a mechanism. Moreover, the co-localisation of proteins recognised by the two antisera in intraparasitic vesicles, indicating that the 32 kDa protein recognised by the two antisera is the same one, is consistent with such a frame-shift mechanism.

Example 3

*Babesia canis* Growth-Inhibition Tests

Inhibition Test by Antisera

Before each experiment, the parasitaemia was adjusted to 1% with a 2% haematocrit (day D0). *B. canis* parasites (in conditions previously described in § growth of *B. canis*) were in vitro cultured in 1 ml for experiments performed in 24 wells plates or in 2 ml for experiments performed in 6 wells plates. The ability of the anti-GST-ORF1 and anti-GST-ORF2 antisera to inhibit *B. canis* growth in vitro was determined by adding each antiserum to the medium at different concentrations (from 1 to 8%). Controls were: i) incubation with the rabbit pre-immune serum or the rabbit anti-GST serum or with the irrelevant rabbit anti-GST-Bcc12D3 serum at same concentrations; ii) a *B. canis* in vitro culture without treatment.

The ability of each concentration of antiserum to inhibit in vitro growth of *B. canis* (isolate A and B), was performed in triplicate and determined by parasitaemia on Giemsa-stained smears or by metabolic labelling with 50 µCi/ml of $[^3H]$-Hypoxanthine in aqueous solution (ICN), after increasing incubation times of 24 h (day D1) and 48 h (day D2) corresponding respectively to about 3 and 6 *B. canis* life cycles. After D1, half of the volume of the wells was collected and the culture medium was entirely removed and replaced by fresh medium supplemented with antiserum (and $[^3H]$-Hypoxanthine for labelling experiment) at the same concentration used at D0. The collected infected erythrocytes (respectively 5 and 20 µl in 24 and 6 wells plates) were pelleted by centrifugation at 1800 g for 5 min. and washed five times in TBS. For the determination of radioactivity incorporation, they were lysed in 500 µl of RIPA buffer and placed 1 h on ice. The lysates were centrifuged at 15000 g (15 min., 4° C.), 2 µl of the supernatant were then added to 2 ml of Emulsifier-Safe (Packard, USA) and the incorporated radioactivity was measured.

In Vitro Inhibition Assay with Purified Immunoglobulins.

Before each experiment, the parasitaemia was adjusted to 1% with a 2% haematocrit (day D0). *B canis* and *B. rossi* parasites were cultured in vitro in 96 wells plates in 100 µl of medium. Antisera used for inhibition assays (anti-GST-Bcvir15, anti-GST-Bcvir15 pre-immune, anti-GST-Bcc12D3, anti-GST-ORF2 antiserum and anti-GST (Respectively indicated as Bcvir15, TO, CONT, orf2 and GST in FIG. 17)) were first purified by FPLC on a HITrap™ Protein G column (Amersham Pharmacia Biotech). Purified immunoglobulins were then dialyzed overnight at 4° C. versus PBS 1× buffer and total immunoglobulins were titrated using the Coomassie Protein Reagent Kit (Pierce, USA). ELISA was used to evaluate the ratio of immunoglobulins directed either against a native GST protein or against each recombinant protein fused to GST by comparison of reactivity of purified immunoglobulins on 0.1 µg of non recombinant GST or 0.1 µg of recombinant proteins coated in wells. All purified immunoglobulin samples were then adjusted at the same concentration of specific anti-GST immunoglobulins with RPMI. The ability of each sample to inhibit in vitro culture of *Babesia canis* or *Babesia rossi* was performed in triplicate with 1, 2, 4, 8 and 10 µg of specific immunoglobulins directed against the non GST part of the recombinant protein used to obtain the antisera.

The growth inhibition was evaluated by metabolic labelling with 50 µCi/ml of [$^3$H]-Hypoxanthine in aqueous solution (ICN), during 24 hours (about 3 cycles of *B. canis* life cycle). Then, the erythrocytes were blocked on a filter and washed using a Scatron apparatus. Afterward, the radioactivity associated with each well was read in 2 ml of Scintillant (Emulsifier Safe™ Packard, USA) by scintigraphy.

Reversion of the Inhibition by Recombinant GST-ORF1 Protein

The ability of the recombinant GST-ORF1 to reverse the inhibitory effect of the anti-GST-ORF1 on growth of *B. canis* was tested on in vitro culture maintained as described above. Different concentrations of recombinant protein in the medium containing 8% of anti-GST-ORF1 were tested: 20 µg/ml and 40 µg/ml. Four controls were used: i) *B. canis* in vitro culture without treatment; ii) culture containing 20 µg/ml or 40 µg/ml of recombinant GST-ORF1; iii) a culture containing 8% of anti-GST-ORF1 antiserum. The ability of each concentration of GST-ORF1 to reverse the inhibitory effect of the anti-GST-ORF1 antiserum was performed in triplicate and determined by parasitaemia on Giemsa-stained smears at D0, D1 and D2 as described above.

Results:

Inhibition test by antisera. In a first experiment, the ability of the different bleedings from the anti-GST-ORF1 antiserum (noted II, III and IV in the FIG. 13) to inhibit the in vitro growth of *B. canis* (isolate A) was tested by adding in the culture medium different concentration of each bleeding (from 1 to 8%, respectively noted A to D in the FIG. 13). Compared to the control culture, where parasitaemia increased from 1 to 35% during the 2 days experiment (FIG. 13E), a significant inhibitory effect of the anti-GST-ORF1 on the in vitro growth of *B. canis* was observed at D2 with the second and the third bleedings of the antiserum at a concentration of 8% since the parasitaemia was of around 15% at D2 in these treated cultures (FIG. 13D, III and IV, respectively).

As control, no inhibitory effect of the pre-immune rabbit serum was observed whatever the concentration used (FIG. 13, I).

Another experiment was performed in order to analyse the inhibitory effect of the anti-GST-ORF2 antiserum on the growth of *B. canis* (FIG. 14). It was tested and compared to anti-GST-ORF1 antiserum, and pre-immune or anti-GST or irrelevant anti-GST-Bcc12D3 rabbit antisera were used as controls (FIG. 14). All antisera were tested at the inhibitory concentration of anti-GST-ORF1 (8%). In that experiment, a significant inhibitory effect of the anti-GST-ORF2 was also observed at D2 since the parasitaemia was of 22% in the treated culture whereas it was of 35% in the control culture. Moreover, the inhibitory effect of anti-GST-ORF2 was found lower than the one observed with the anti-GST-ORF1 (at D2 the parasitaemia is of around 15%). No inhibitory effect was observed by treating the culture with 8% of pre-immune or anti-GST or anti-GST-Bcc12D3 rabbit antisera.

The 8% inhibitory effect of the anti-GST-ORF1 antiserum was also checked by measuring incorporation of [$^3$H]-Hypoxanthine following metabolic labelling of treated and untreated cultures, and the experiment was performed on the isolates A and B of *B. canis* (FIG. 15, A and B respectively). For both isolates and compared to the control cultures, a significant inhibitory effect was observed at D2 since the radioactivity was of around 2000 cpm in the untreated cultures and respectively of 250 and 350 cpm in the isolate A and B. In contrast to parasitaemia counting which was unable to detect an inhibitory effect of the anti-GST-ORF1 at D1, this inhibitory effect was visible at this day by radioactivity counting. Indeed, radioactivity in the control culture was of 1000 cpm whereas in treated cultures it was of 200 and 250 cpm respectively in the isolate A and B.

In Vitro Inhibition Assay with Purified Immunoglobulins.

The experiment described above was repeated with purified immunoglobulins, in order to exclude non-immunoglobulin serum-components as a possible non-specific cause of growth inhibition. As is shown in FIG. 17, purified immunoglobulins are capable of inhibiting in vitro growth of both *Babesia canis* A and B.

Surprisingly, this implies that vaccines comprising one or both proteins according to the invention are capable of inhibiting parasitic growth of *B. canis* in general, regardless the serovar. As expected, in vitro growth of *B. rossi* M is not inhibited.

Reversion of the inhibition. In order to confirm the inhibitory effect of anti-GST-ORF1 on the in vitro growth of *B. canis*, an experiment was conducted to reverse this effect by adding in the culture different concentration of purified recombinant GST-ORF1 (FIG. 16). The two concentrations used were 20 and 40 µg/ml of GST-ORF1. This experiment showed that addition of GST-ORF1 protein in the medium of a culture treated with 8% of anti-GST-ORF1 allowed a 50 and 100% reversion of the inhibition process respectively at concentration of 20 and 40 µg/ml (FIG. 16, C and D respectively). Such a concentration of GST-ORF1 added in a non treated culture had no effect on the growth of the parasite (FIG. 16, A and B respectively). Untreated culture and a treated culture with 8% of anti-GST-ORF1 were used as controls for this experiment (FIG. 16, E and F, respectively).

Conclusion: Both anti-GST-ORF1 and anti-GST-ORF2, at a concentration of 8% were able to inhibit, significant and specifically, the in vitro growth of *B. canis* isolate. This effect was already observed at D1. A concentration of 40 µg/ml of recombinant GST-ORF1 was able to totally reverse this inhibitory effect. Moreover, filtration of anti-GST-ORF1 and anti-GST antisera indicated that 8% of each antiserum represents a respective concentration of immunoglobulins of 100 and 50 µg/ml of culture (data not shown). An ELISA test, performed on coated recombinant GST, indicated that half of the immunoglobulins from the anti-GST-ORF1 were directed against the GST part of the recombinant GST-ORF1 (data not shown), it means that the inhibitory effect observed at 8% of anti-GST-ORF1 on the in vitro growth of *B. canis* was obtained by 50 µg/ml of immunoglobulins specifically directed against the protein Bcvir15. At least, this is consistent with the 40 µg of recombinant GST-ORF1 necessary to reverse the inhibitory effect of the antiserum anti-GST-ORF1.

Thus, these data indicated that Bcvir15 and Bcvir32 (products of the BCVIR cDNA), for which the genetic information is present in *B. canis* but not encoded by the *B. canis* genomic DNA play an important role in the virulence of the Apicomplexan parasite *B. canis*. Vaccines based upon these proteins or nucleic acid sequences encoding these proteins are shown to play an important role in the inhibition of *B. canis* parasite growth, regardless the serovar.

A: Schematic representation of entire BCVIR cDNA with predicted ORFs represented by boxes and sequence derived primers represented with arrows.

B: Representation of the predicted overlapping sequence (SEQ ID NO.: 11) and its deduced amino acid sequences ORF2 (SEQ ID NO.: 17) and ORF1 (amino acids 123-141 of SEQ ID NO.: 2).

FIG. 2: Nucleic sequence of the complete BCVIR cDNA (SEQ ID NO.: 1) and deduced amino acid sequence (SEQ ID NO.: 2) of the Bcvir15.

The common amino acid sequence between Bcvir15 and the putative Bcvir32 is represented in regular upper case. A GRAM-positive anchoring hexapeptide is overlined. The overlapping sequence between the two predicted ORF of BCVIR cDNA are indicated in bold italic. Cloning restriction sites are in bold case.

FIG. 3: Nucleic sequence of the complete BCVIR cDNA (SEQ ID NO.: 3) and deduced amino acid sequences of the putative Bcvir32 protein (SEQ ID NO.: 4).

The overlapping region between ORF1 and ORF2 of the BCVIR cDNA is indicated in bold italic. Cloning restriction sites are in bold case.

Figure 1:
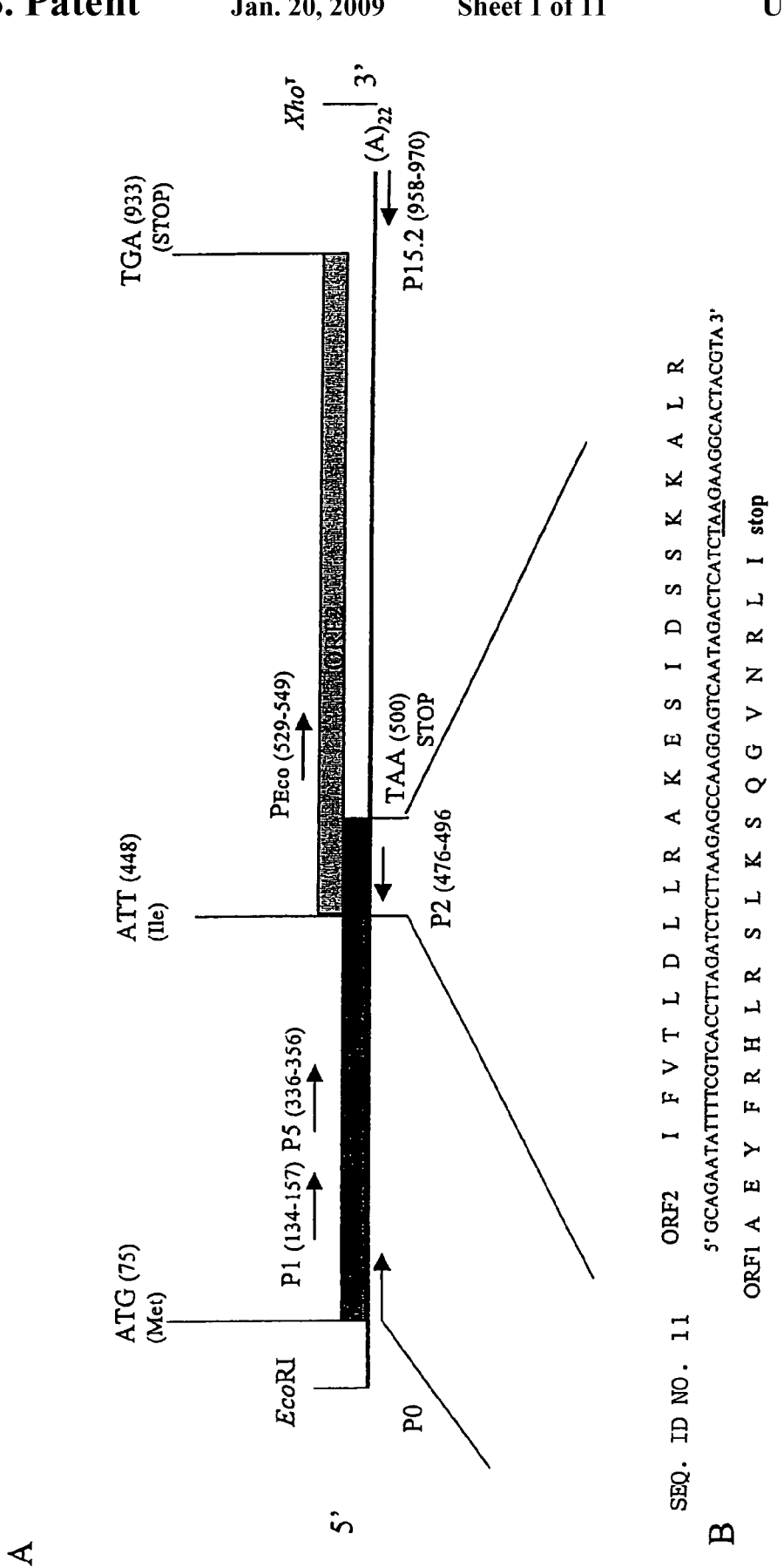
FIG. 1: Schematic representation of the BCVIR cDNA
Figure 4:
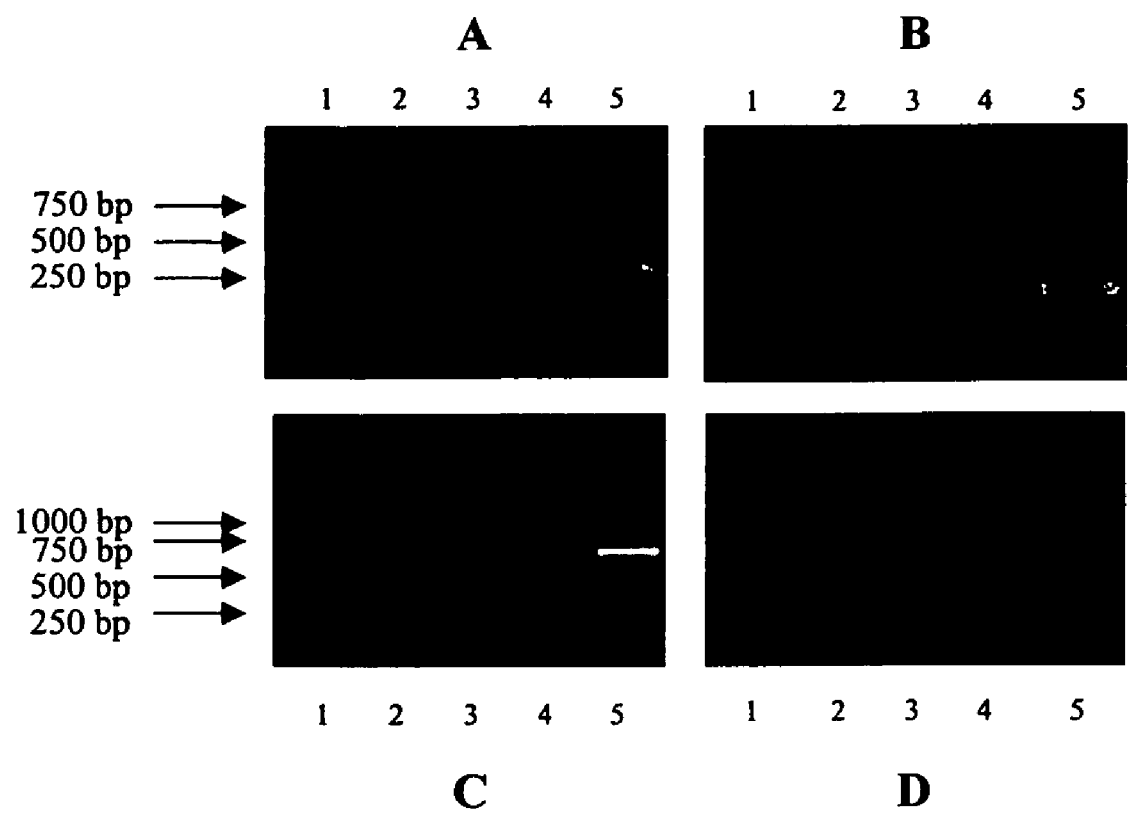

FIG. 4: PCR analysis of BCVIR cDNA sequence on genomic DNA of *B. canis*

Genomic DNA analysed were extracted from isolate A of *B. canis* (lane 1), isolate B of *B. canis* (lane 2), isolate F of *B. rossi* (lane 3) and uninfected dog blood sample (lane 4). The pBK-CMV plasmid carrying the BCVIR cDNA sequence was used as positive control (lane 5). PCR were performed using the combination of primers P1/P2 (A), P5/P2 (B), P5/P15.2 (C) and Bcc12D3.1/Bcc12D3.2 (D)

Figure 5:
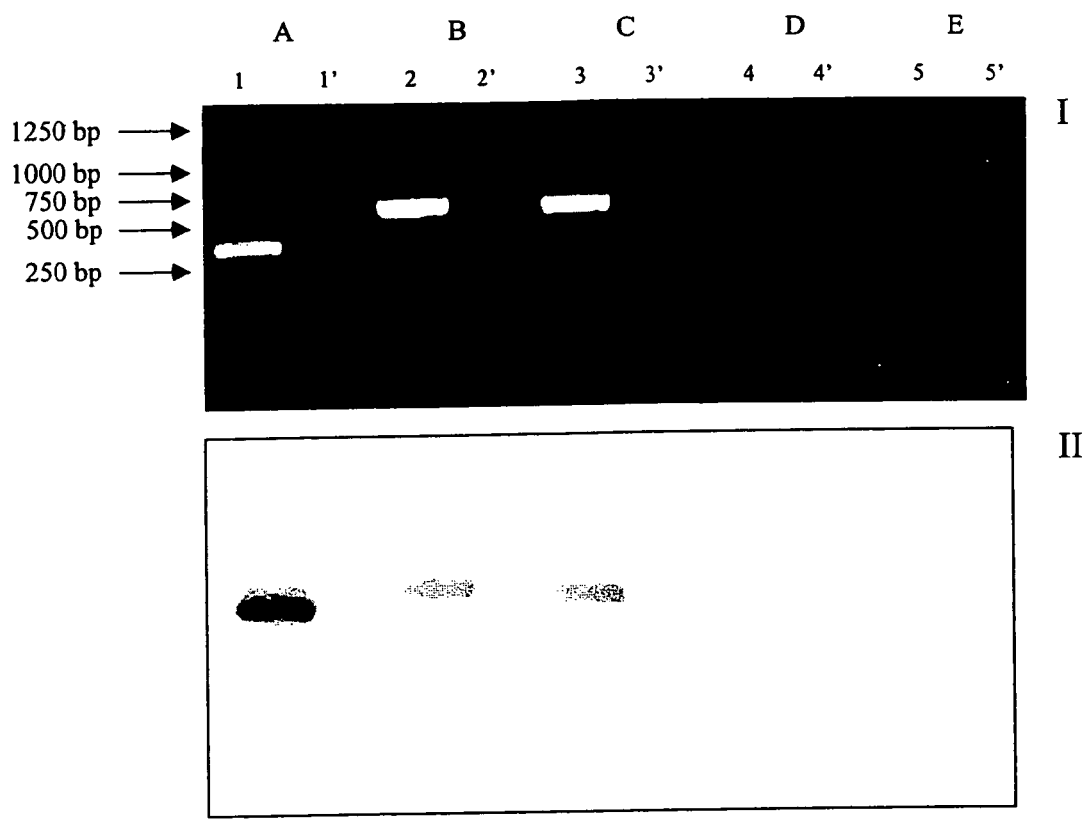

FIG. 5: RT-PCR analysis of the BCVIR sequence

The experiment was performed on total RNA isolated from *B. canis* (isolate A). P1 (lane 1), P5 (lane 2), P15.2 (lane 3); all derived from BCVIR sequence and Bcc12D3.1 (lane 4) or Bcc12D3.2 (lane 5) of Bcc12D3 sequence were used as initial primers for the retrotranscription step. The first step of retrotranscription was performed either with eAMV-RT enzyme (lane 1-5) or without eAMV-RT enzyme as control (lane 1'-5'). The second step of amplification was performed by PCR with the combination of primers P1/P2 (A), P5/P15.2 (B, C) and Bcc12D3.1/Bcc12D3.2 (D). Amplified products were separated on 0.8% agarose gel and visualised by Bet staining under UV light (I) or they were transferred on to Nitrocellulose membrane and hybridised with a total BCVIR cDNA sequence used as a probe in order to check the specificity of the amplified PCR products (II).

Figure 6:
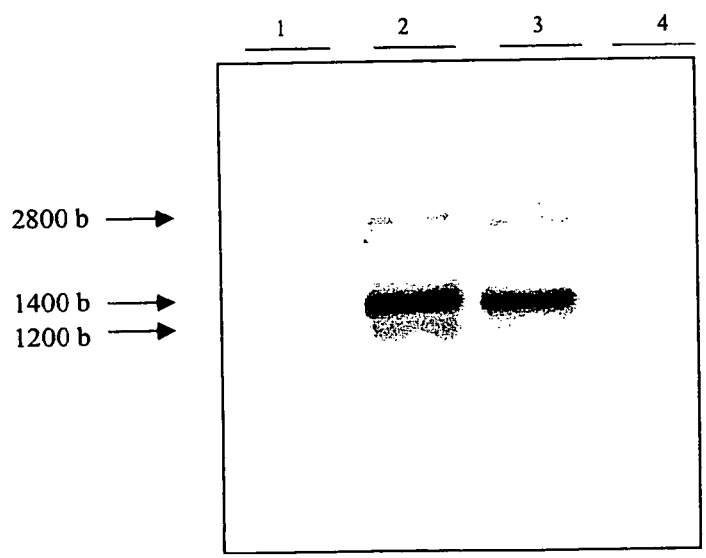

FIG. 6: Northern blot analysis of the BCVIR cDNA sequence

Hybridisation was performed using the PCR derived P1/P2 probe of BCVIR cDNA sequence on total RNA from the isolate Rouen 1987 of *B. divergens* (lane 1), total RNA from the isolate A of *B. canis* (lane 2), non messenger RNA from the isolate A of *B. canis* (lane 3) and total RNA the isolate F of *B. rossi* (lane 4).

Figure 7:
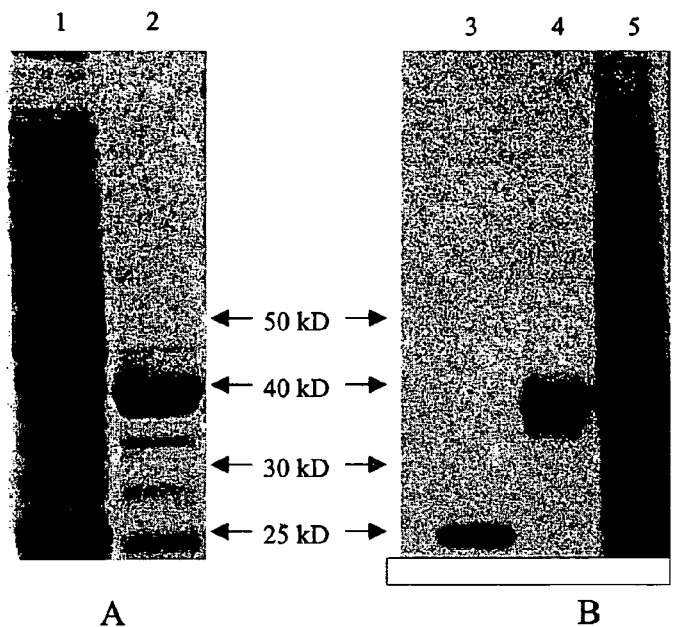

FIG. 7: Over expression and purification of the GST-ORF1 and GST-ORF2 recombinant proteins from *E. coli*

Proteins were purified from BL21 (DE3) cells after 3 h IPTG induction as described, separated on a SDS/12% polyacrylamide gel, and stained with Coomassie brilliant blue. Lanes: 1A, *E. coli* expressing GST-ORF1 lysate; 1B, purified GST-ORF1; 3B control purified native GST; 4B purified GST-ORF2; inclusion bodies lysate from *E. coli* expressing GST-ORF2.

Figure 8:
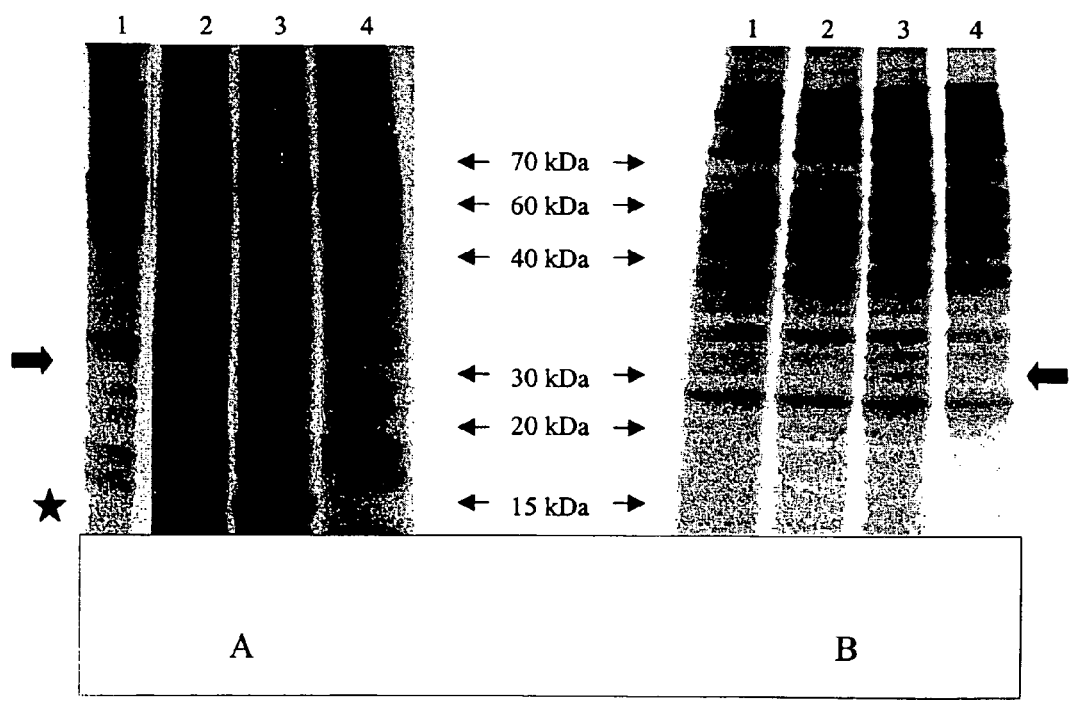

FIG. 8: Immunoprecipitation of [$^{35}$S] methionine labelled *Babesia canis* isolate A antigens Radiolabelled Total antigens (A) or Exoantigens (B) were immunoprecipitated respectively by rabbit pre-immune sera (1), anti-GST rabbit polyclonal serum (2), anti-GST-ORF1 rabbit polyclonal serum (3) and anti-GST-ORF2 rabbit polyclonal serum. Asterisk and arrows indicate respectively the location of the Bcvir15 and the putative Bcvir32.

Figure 9:
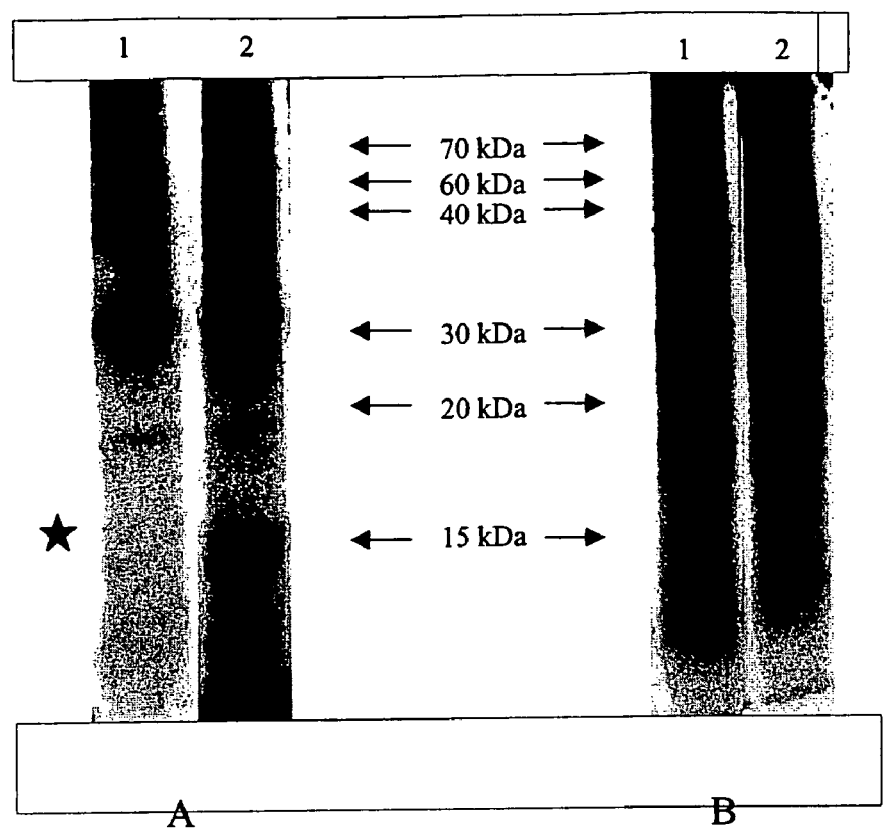

FIG. 9: Immunoprecipitation of [$^{35}$S] methionine Labelled *Babesia canis* A Strain TX-114 Partitioned Antigens The [$^{35}$S] methionine labelled in vitro cultures of *Babesia canis* A isolate were solubilized in TX-114, and after a phase separation, the hydrophilic were recovered in the aqueous phase and the amphiphilic antigens were recovered in the detergent phase. Pre-immune rabbit serum (1) or anti-GST-ORF1 rabbit polyclonal serum (2) were used to immunoprecipitated either the aqueous-phase proteins (A) or the detergent phase proteins (B). Arrow indicate the location of the Bcvir15.

Figure 10:
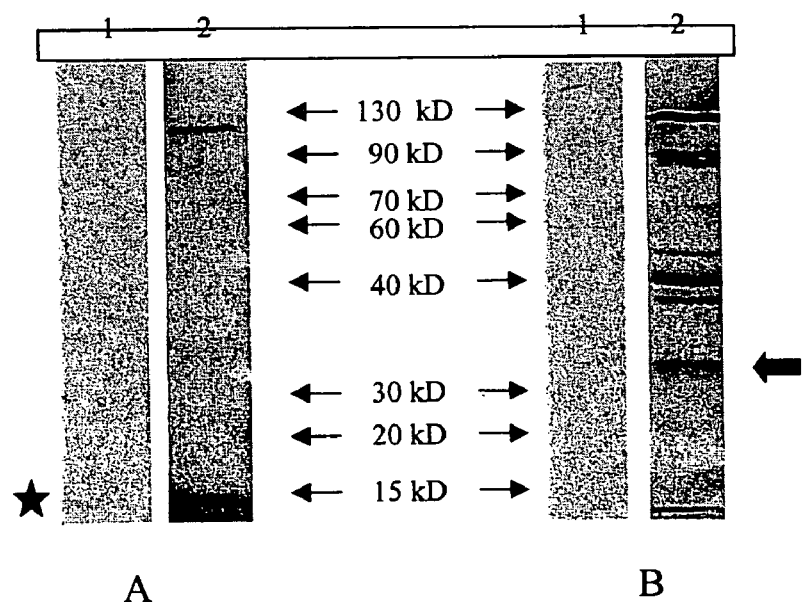

FIG. 10: Immunoblot analysis of SDS-PAGE separated *Babesia canis* merozoite antigens The experiment was performed on purified merozoites of the isolate A of *Babesia canis*. Antigens were separated on a 12% SDS/polyacrylamide gel and transferred onto nitrocellulose sheets. Incubation was done at a 1:100 dilution with pre-immune rabbit serum (1A and 1B), with anti-GST-ORF1 rabbit polyclonal serum (2A) or with anti-GST-ORF2 rabbit polyclonal serum (2B). The position of the Bcvir15 and Bcvir32 are indicated respectively by an asterisk and an arrow.

Figure 11:
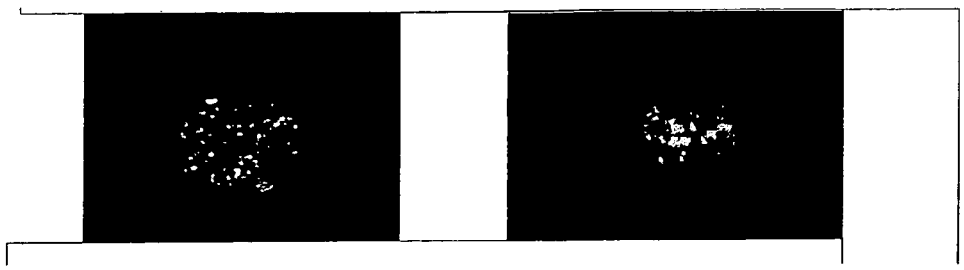

FIG. 11: Localisation of BCVIR sequence expressed products.

IFA tests were performed with the isolate A of *Babesia canis*.

(A) fluorescence associated with anti-GST-ORF1

(B) fluorescence associated with anti-GST-ORF2

Figure 12:
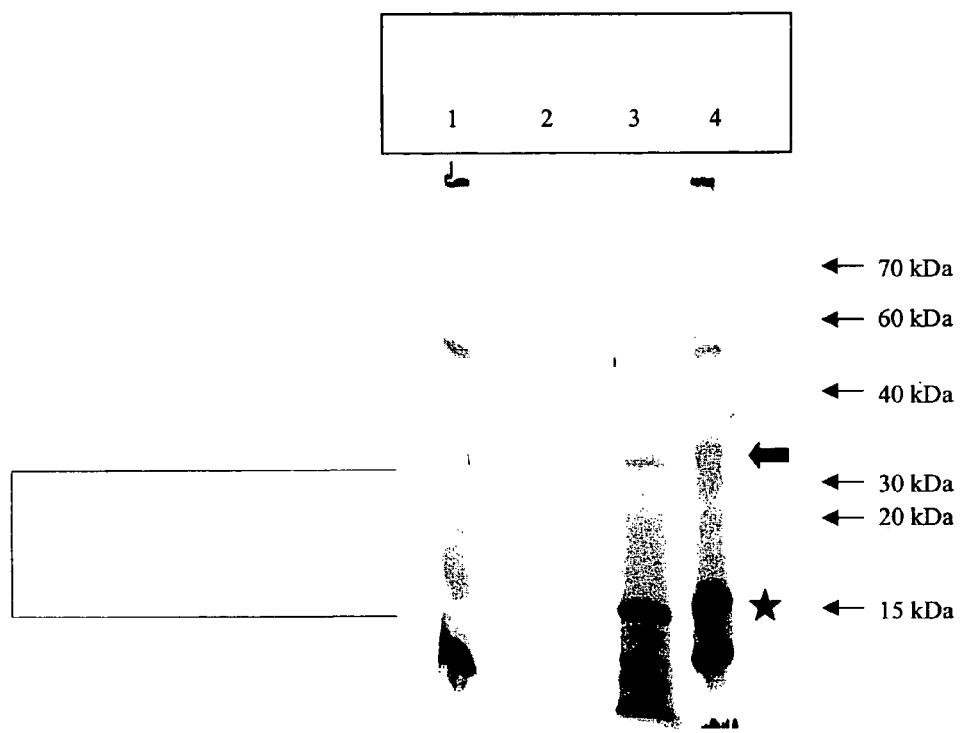

FIG. 12: Analysis of in vitro translated products.

Radiolabelled In vitro products translated from P0/P15.2 PCR amplification on pBK-CMV BCVIR cDNA were separated on a 12% SDS-PAGE. Total products (4) or products immunoprecipitated by anti-GST-ORF1 (3) were analysed. Total expression product of reticulocyte lysate without DNA (1) or immunoprecipitated product from a reticulocyte lysate without DNA (2) were used as controls. Asterisk localise Bcvir15 and arrow localise Bcvir32.

Figure 13:
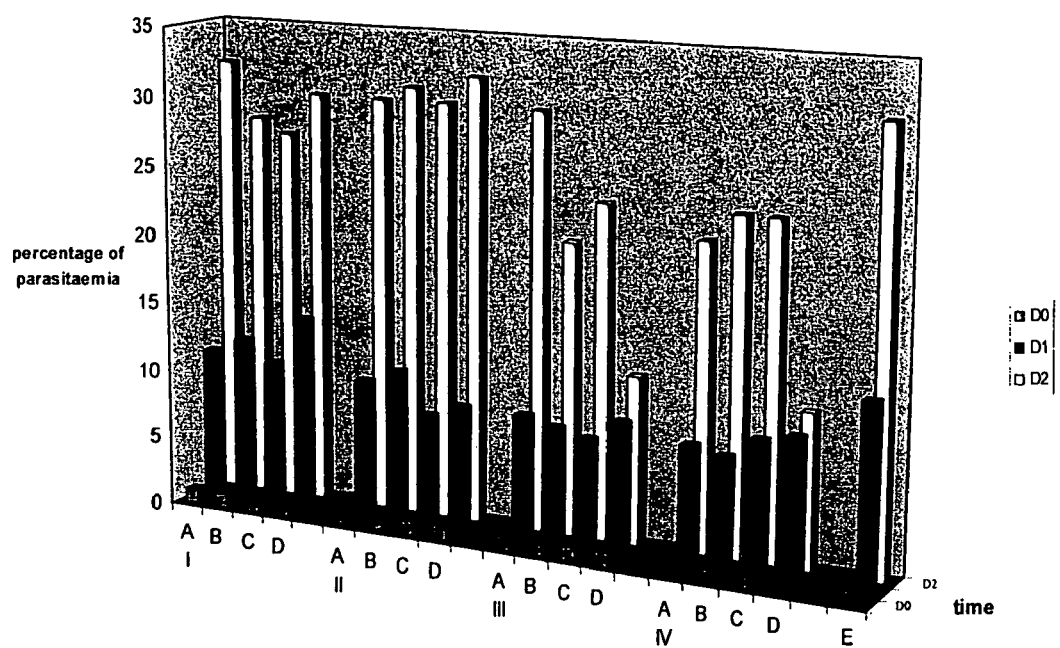

FIG. 13: evaluation of the capacity of different concentration of anti-GST-ORF1 rabbit polyclonal sera to inhibit *Babesia canis* A strain in vitro culture.

Different bleeding (respectively first (II), second (III) and third (IV) anti-GST-ORF1 rabbit polyclonal serum were added at a final concentration of 1% (A), 2% (B), 4% (C) and 8% (D) to *Babesia canis* A in vitro culture. Pre-immune serum (I) was used as control as was culture maintained in standard conditions (E)

Figure 14:
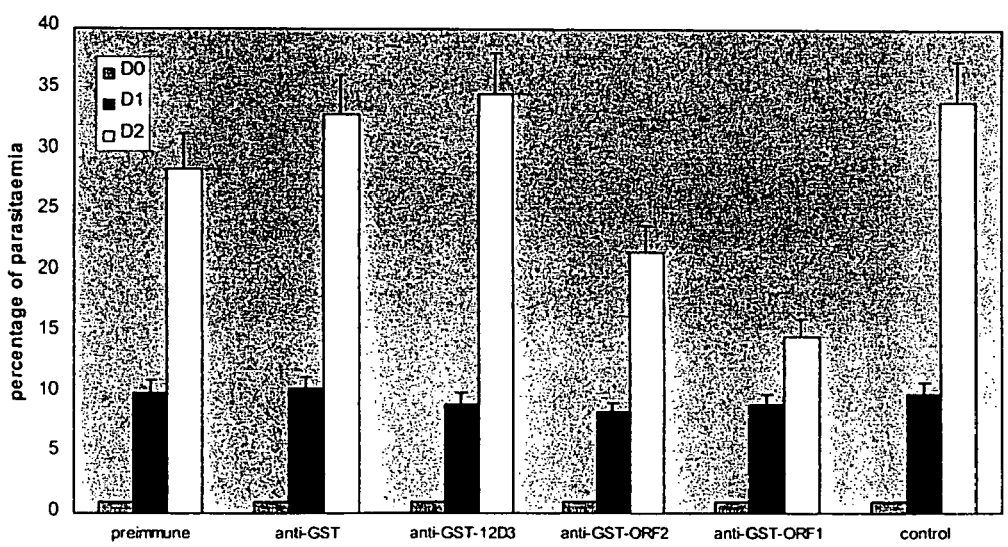

FIG. 14: Inhibition of *Babesia canis* A strain In vitro culture by different rabbit polyclonal sera Sera were tested for their ability to inhibit parasite growth when added at a rate of 8% on *Babesia canis* A strain in vitro culture. D0, D1, D2 indicate respectively parasitaemia values at the start of the test, after 24 hours of culture growth and after 48 hours of culture growth. Tested sera were rabbit polyclonal anti-GST-ORF1 and anti-GST-ORF2 and control sera were rabbit pre-immune serum, rabbit polyclonal anti-GST and rabbit polyclonal anti-GST-Bcc12D3. Control lane indicate culture in standard conditions without addition of any rabbit serum.

Figure 15:
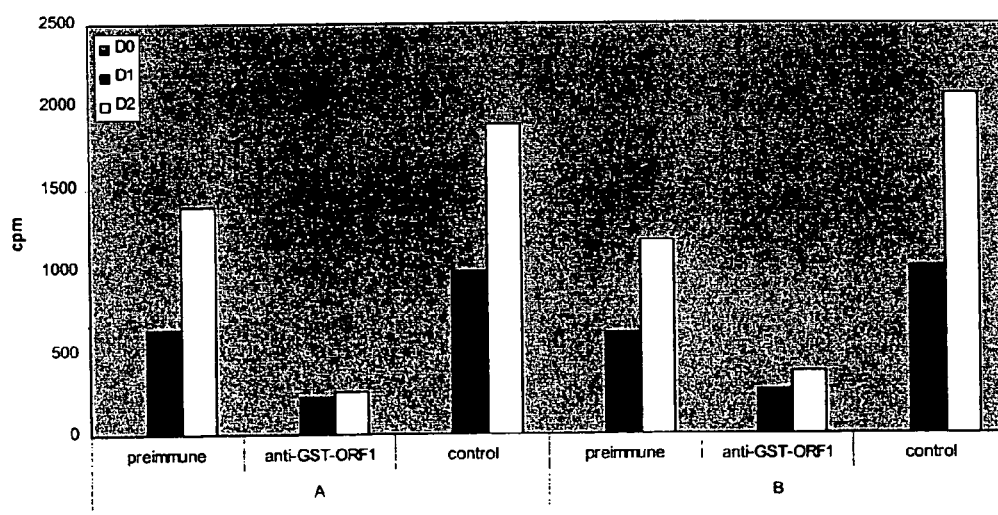

FIG. 15: Inhibition test of *Babesia canis* in vitro culture evaluated by [$^3$H] hypoxanthine metabolic labelling Anti-GST-ORF1 and control pre-immune rabbit sera were all tested at 8% final concentration on *Babesia canis* A strain (I) and *Babesia canis* B strain (II). Control lane indicate in both case parasites grown in standard conditions.

Figure 16:
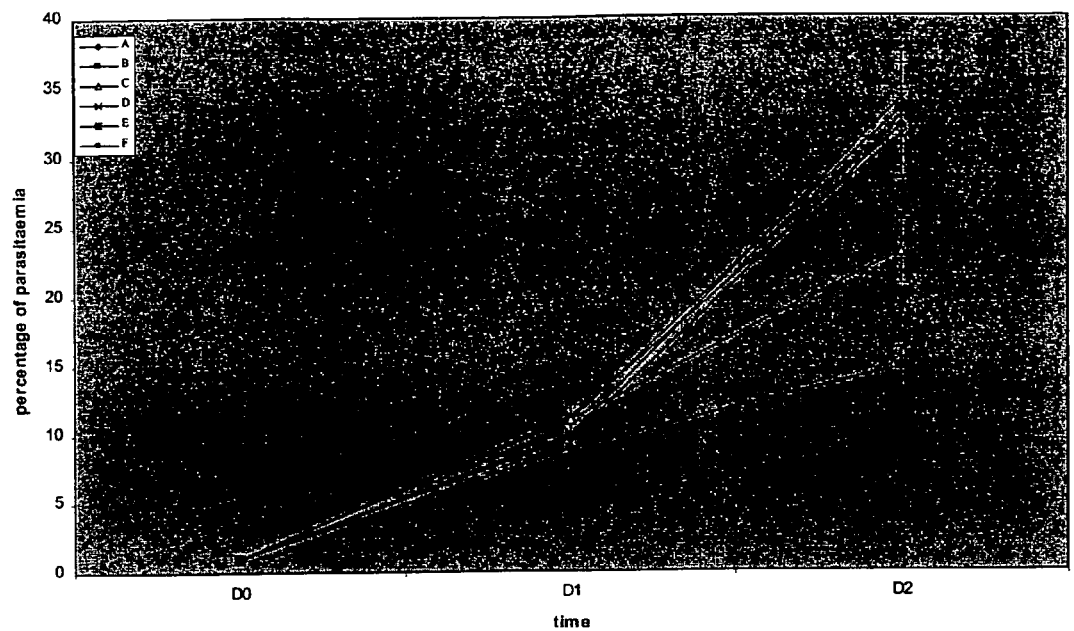

FIG. 16: Inhibition test against GST-ORF1 recombinant protein

The recombinant GST-ORF1 protein was tested for its ability to revert the capacity of rabbit polyclonal anti-GST-ORF1 serum to inhibit *Babesia canis* A strain growth in vitro. The protein was tested at 20 µg/ml (C) or 40 µg/ml (D) against 8% of anti-GST-ORF1 rabbit polyclonal serum. Controls were protein alone added in the culture at a rate of 20 µg/ml (A) or 40 µg/ml (B), culture in standard conditions (E) and culture with 8% of anti-GST-ORF1 rabbit polyclonal serum (F)

FIG. 17: Inhibition test of *Babesia canis* in vitro culture with purified immunoglobulins evaluated by [$^3$H] hypoxanthine metabolic labelling. The ability of purified immunoglobulins (anti-GST-Bcvir15, anti-GST-Bcvir15 pre-immune, anti-GST-Bcc12D3, anti-GST-ORF2 antiserum and anti-GST (Respectively indicated as Bcvir15, T0, CONT, orf2 and GST in FIG. 17) to inhibit in vitro culture of *Babesia canis* or *Babesia rossi* was performed in triplicate with 1, 2, 4, 8 and 10 µg of specific immunoglobulins. Growth inhibition was evaluated by metabolic labelling with 50 µCi/ml of [$^3$H]-Hypoxanthine.

We claim:

1. An isolated *Babesia canis* protein, said protein having a molecular weight of 32 kD and comprising the amino acid sequence SEQ ID NO: 4.

2. An antigenic composition comprising the protein of claim 1 and a pharmaceutically acceptable carrier.

3. The antigenic composition of claim 2, further comprising an adjuvant.

4. The antigenic composition of claim 2, further comprising an additional antigen selected from the group consisting of *Ehrlichia canis, Babesia gibsoni, vogeli, rossi, Leishmania donovani*-complex, Canine parvovirus, Canine distempervirus, *Leptospira interrogans serovar canicola, icterohaemorrhagiae, pomona, grippotyphosa, bratislava*, Canine hepatitisvirus, Canine parainfluenzavirus, rabies virus, *Hepatozoon canis* and *Borretia burgdorferi*.

5. A vaccine comprising the *Babesia canis* protein according to claim 1.

6. A vaccine for combating *Babesia canis* infections, comprising a protein according to claim 1 and a pharmaceutically acceptable carrier.

7. A vaccine according to claim 6, further comprising an adjuvant.

8. A vaccine according to claim 6, further comprising an additional antigen selected from the group consisting of *Ehrlichia canis, Babesia gibsoni, vogeli, rossi, Leishmania donovani*-complex, Canine parvovirus, Canine distempervirus, *Leptospira interrogans serovar canicola, icterohaemorrhagiae, pomona, grippotyphosa, bratislava*, Canine hepatitisvirus, Canine parainfluenzavirus, rabies virus, *Hepatozoon canis* and *Borrelia burgdorferi*.

9. A method of manufacturing a vaccine, comprising mixing a pharmaceutically acceptable carrier and a protein according to claim 1.

* * * * *